(12) United States Patent
Legrand et al.

(10) Patent No.: US 7,179,300 B2
(45) Date of Patent: Feb. 20, 2007

(54) COSMETIC COMPOSITION CONTAINING SULFINIC ACID DERIVATIVES

(75) Inventors: Frédéric Legrand, Courbevoie (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 330 days.

(21) Appl. No.: 10/489,733

(22) PCT Filed: Sep. 11, 2002

(86) PCT No.: PCT/FR02/03093

§ 371 (c)(1),
(2), (4) Date: Sep. 28, 2004

(87) PCT Pub. No.: WO03/041668

PCT Pub. Date: May 22, 2003

(65) Prior Publication Data

US 2005/0050648 A1     Mar. 10, 2005

(30) Foreign Application Priority Data

Sep. 17, 2001  (FR)  ................................. 01 11994

(51) Int. Cl.
*D06L 3/00* (2006.01)
(52) U.S. Cl. ....................... 8/101; 8/107; 8/110; 8/405; 8/455; 132/202; 132/208; 424/70.1; 424/70.2; 424/70.5
(58) Field of Classification Search .................... 8/101, 8/107, 405, 455; 132/202, 208; 424/70.1, 424/70.2, 70.5
See application file for complete search history.

(56) References Cited

U.S. PATENT DOCUMENTS 3,892,845 A    7/1975   Cunningham et al.
6,211,400 B1 *  4/2001   Berghofer et al. .......... 560/150

FOREIGN PATENT DOCUMENTS

GB           855 496        11/1960

OTHER PUBLICATIONS

STIC Search Report dated Sep. 28, 2006.*

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The invention relates to a cosmetic composition which is intended, in particular, for bleaching human keratin fibers, particularly hair, which have been dyed with oxidation dyes and/or direct dyes. The inventive composition comprises sulphunic acid derivatives having general formula (I) in a cosmetically-acceptable medium, at a pH of between 1.5 and 9. The invention also relates to novel compounds having formula (I), the devices comprising several compartments which are used to dye and bleach the aforementioned fibers and the bleaching method using said composition

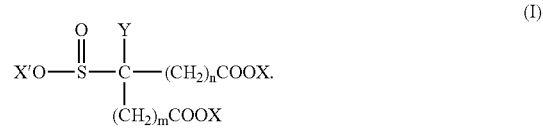

43 Claims, No Drawings

COSMETIC COMPOSITION CONTAINING SULFINIC ACID DERIVATIVES

This application constitutes the national stage filing for PCT Application No. PCT/FR02/03093, filed Sep. 11, 2002, which claims priority to FR 01/11994, filed Sep. 17, 2001, both of which are incorporated herein by reference.

The invention relates to a cosmetic composition comprising at least one sulfinic acid derivative of formula (I) defined below, and especially a composition for bleaching human keratin fibers, in particular the hair, dyed with oxidation dyes and/or direct dyes. The invention also relates to the novel compounds of formula (I), to their use as dye-reducing agents in compositions for bleaching at a pH of between 1.5 and 9 and preferably between 1.8 and 6, and to human keratin fibers dyed with oxidation dyes and/or direct dyes. The invention also relates to multi-compartment devices for dyeing and bleaching said fibers and to the bleaching process using this composition.

It is known practice to dye keratin fibers, and in particular human hair, with dye compositions containing oxidation dyes and/or direct dyes.

The dyeing performed with oxidation dyes, or "oxidation dyeing", is permanent dyeing; it comprises as oxidation dyes, oxidation dye precursors and couplers.

The oxidation dye precursors, which are commonly known as "oxidation bases", are compounds that are initially colorless or weakly colored, which develop their dyeing power on the hair in the presence of oxidizing agents added at t he time of use, leading to the formation of colored compounds and dyes. The formation of these colored compounds and dyes results either from an oxidizing condensation of the "oxidation bases" with themselves, or from an oxidizing condensation of the "oxidation bases" with coloration modifiers, which are commonly known as "couplers" and which are generally present in the dye compositions used in oxidation dyeing.

The oxidation bases are in particular ortho- or para-phenylenediamines, ortho- or para-aminophenols and heterocyclic bases.

The couplers are chosen especially from aromatic meta-diamines, meta-aminophenols, meta-diphenols and certain heterocyclic compounds.

The variety of molecules used as oxidation bases and couplers allows a wide range of colors to be obtained.

To vary the shades obtained with said oxidation dyes, or to enrich them with glints, direct dyes may be added thereto.

The dyeing performed with direct dyes gives a semi-permanent or temporary coloration; direct dyes give the natural color of the hair a more or less pronounced color change that may be resistant to shampooing several times.

These direct dyes may be used without oxidizing agent.

The direct dyes conventionally used are chosen especially from nitrobenzene direct dyes, azo direct dyes, quinone and in particular anthraquinone direct dyes, azine direct dyes, triarylmethane direct dyes, indoamine direct dyes and natural direct dyes.

More recently, in patent applications WO-95/15144, WO-95/01772 and EP-1 025 834, it has been recommended to use novel cationic direct dyes that differ from standard direct dyes in the very chromatic shades they give to keratin fibers.

Said cationic direct dyes may be used in oxidizing medium.

In the presence of an oxidizing agent, the aim is to obtain lightening dyeing. Lightening dyeing is performed by applying to the hair an extemporaneous mixture of the cationic direct dye and of an oxidizing agent, and makes it possible especially to obtain, by lightening the melanin of the hair, an advantageous effect such as a unified color in the case of gray hair, or to bring out the color in the case of naturally pigmented hair.

However, for various reasons, such as the wish to partially or totally modify the shade thus given to the head of hair by an oxidation dyeing, direct dyeing or lightening dyeing operation, or the wish to remove this coloration (which is referred to as stripping), there may arise the desire to partially or totally destroy the pigments thus formed or placed in or on the hair.

This bleaching has been performed hitherto via processes using oxidizing or reducing systems.

In the oxidizing systems, the oxidizing agents conventionally used are hydrogen peroxide or compounds capable of producing hydrogen peroxide by hydrolysis, such as urea peroxide or persalts, for instance perborates, percarbonates and persulfates, hydrogen peroxide and persulfates being particularly preferred.

Among the reducing systems, it is known practice, from German patent 1 151 242, to use hydroxymethanesulfinic acid at a pH of between 7 and 9, to bleach dyed hair. It is also known practice to use sodium sulfite ($Na_2SO_3$), in patents U.S. Pat. Nos. 2,149,319 and 3,838,966 and patent application JP-04 356 413A.

A process for bleaching dyed keratin fibers is also described in patent U.S. Pat. No. 3,892,845 and consists in applying to the fibers an aqueous composition comprising a combination of two types of reducing agent, a dye-reducing agent and an agent for reducing the disulfide covalent bonds of keratin; the dye-reducing agent is a zinc, potassium, sodium or calcium hydroxymethanesulfinate or hydrosulfite and the keratin-reducing agent is especially thioglycolic acid, a potassium or sodium bisulfate or bisulfite, potassium disulfide, thiourea or certain phosphorus compounds.

However, it is also known practice to bleach human keratin fibers such as the hair, and in particular hair artificially dyed with oxidation dyes, using reducing agents at acidic pH.

The technique of bleaching by reduction at acidic pH has the advantage of sensitizing the hair fibers less and of not lightening the natural base of the hair.

Thus, commercial products use sodium hydroxymethanesulfinate as dyed-hair-reducing agent at acidic pH.

Furthermore, it has recently been recommended, in patent application EP-0 943 316, to use a combination at acidic pH comprising ascorbic acid and α-oxocarboxylic acid to bleach human hair that has been dyed beforehand with an oxidation dye, and a commercial hair-bleaching product comprises ascorbic acid and α-ketoglutaric acid.

However, the Applicant has found that none of these prior art techniques produces a sufficiently efficient bleaching of keratin fibers dyed with standard oxidation dyes and/or direct dyes.

Specifically, the bleaching is of poor efficiency, or is even inefficient, with respect to certain shades, such as the fundamental shades and shades with golden and ash glints. In addition, this type of bleaching does not make it possible to sufficiently strip keratin fibers dyed with very chromatic cationic direct dyes especially such as those recently disclosed in patent applications WO-95/15144, WO-95/01772 and EP-1 025 834.

Moreover, sodium hydroxymethanesulfinate generates formaldehyde, which is unfavourable with respect to the harmlessness of the products.

The Applicant has now discovered, entirely surprisingly and unexpectedly, that compounds of formula (I) described below very significantly improve the bleaching of human keratin fibers that have been dyed beforehand with standard oxidation dyes and/or direct dyes, and allow a very much wider range of colors to be removed.

Even more particularly, it has now become possible to partially or totally bleach keratin fibers dyed with cationic direct dyes such as those described above.

These discoveries thus form the basis of the present invention.

A first subject of the invention is thus a cosmetic composition, characterized in that it comprises, in a cosmetically acceptable medium at a pH of between 1.5 and 9, at least one sulfinic acid derivative of formula (I) below:

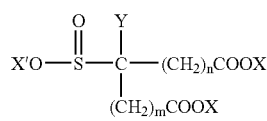

(I)

in which:
X and X', which may be identical or different are chosen from the group formed by a hydrogen atom, a monovalent metal ion or an ionic equivalent of a divalent metal from groups Ia, IIa, IIb, IVa and VIIIb of the Periodic Table of Elements,
Y is chosen from the group formed by an OH radical, a radical $NR_1R_2$ in which $R_1$ and $R_2$, which may be identical or different, denote a hydrogen atom or a $C_1$–$C_6$ alkyl radical,
n and m, which may be identical or different, denote an integer ranging from 0 to 2.

In one particularly preferred form, the pH is between 1.8 and 6.

A second subject of the invention is the use of the compounds of formula (I) thus defined, as dye-reducing agent, in an aqueous cosmetic medium that is suitable for bleaching, at a pH of between 1.5 and 9 and preferably between 1.8 and 6, human keratin fibers dyed with oxidation dyes and/or direct dyes, in particular the hair.

A third subject of the invention is a composition for bleaching human keratin fibers dyed with the oxidation dyes and/or direct dyes, in particular the hair, comprising at least one dye-reducing agent in an aqueous cosmetic medium that is suitable for bleaching at a pH of between 1.5 and 9 and preferably between 1.8 and 6, and characterized in that said reducing agent is a sulfinic acid derivative of formula (I) defined above.

Said bleaching may be partial or total.

Said compounds of formula (I) also have the advantage of not generating formaldehyde.

The compositions for bleaching the hair using reducing agents are mainly in the form of ready-to-use compositions consisting of anhydrous products (powders) or creams or gels containing the reducing agent(s), which are mixed at the time of use with an aqueous composition containing a pH agent. The bleaching compositions are also in the form of aqueous ready-to-use compositions containing the reducing agent(s) at the appropriate pH.

The composition according to the invention is a ready-to-use composition.

For the purposes of the invention, the expression "ready-to-use composition" means the composition intended to be applied in unmodified form to the keratin fibers, i.e. it may be stored in unmodified form before use or may result from the extemporaneous mixing of two or more compositions.

The sulfinic acid derivatives of formula (I) according to the invention are novel compounds.

A fourth subject of the present invention is thus the novel compounds of formula (I).

The sulfinic acid derivatives of formula (I) for which Y denotes an OH radical may be obtained by reacting, under an inert atmosphere, sodium dithionite (in the case where X denotes Na$^+$) with the corresponding oxocarboxylic acid (or the salt thereof), according to the following scheme:

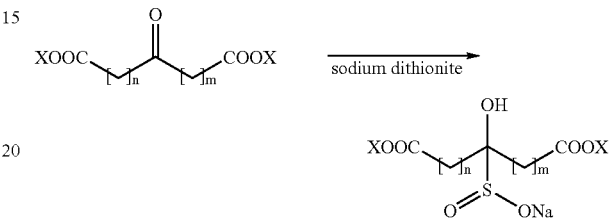

The sulfinic acid derivatives of formula (I) for which Y denotes a radical $NR_1R_2$ may be obtained according to a Mannich reaction, by reacting, in basic medium, a substituted or unsubstituted amine with the corresponding hydroxysulfinate.

This reaction may be performed in two stages, or in a single stage starting with the corresponding oxocarboxylic acid (or a salt thereof), by adding thereto the sodium dithionite and the corresponding amine, according to the following scheme:

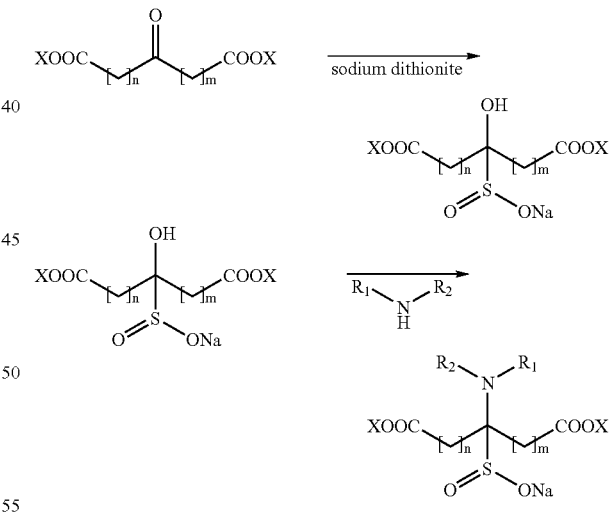

The sulfinic acid derivatives of formula (I) may be present in the bleaching composition according to the invention in proportions of between 0.01% and 20% and preferably between 0.1% and 10% by weight relative to the total weight of the composition.

According to the present invention, the sulfinic acid derivatives of formula (I) for which:
m=0,
X and X', which may be identical or different, are chosen from a hydrogen atom, an alkali metal ion and an ionic equivalent of an alkaline-earth metal or of zinc, Y is an OH radical or an NH$_2$ radical,
n=0, 1, 2, are preferred.

It is even more particularly preferred to use the compounds of formula (I) for which X and X' denote the ion Na, Y denotes OH, m=0, and n=0, 1, 2.

A subject of the invention is also multi-compartment packaging "kits" or devices intended (i) for dyeing and then (ii) for bleaching keratin fibers dyed with oxidation dyes and/or direct dyes, in particular human keratin fibers such as the hair, characterized in that they comprise a first compartment comprising a composition for the oxidizing dyeing or non-oxidizing dyeing of said fibers, and, in a second compartment, a composition for the reductive bleaching of said dyed fibers comprising at least one compound of formula (I) described above at a pH of between 1.5 and 9 and preferably between 1.8 and 6.

The invention is also directed toward a process for bleaching keratin fibers dyed with oxidation dyes and/or direct dyes, in particular human keratin fibers such as the hair, using a bleaching composition as described above.

In a first compartment of the kit, the oxidizing dye may be a standard oxidation dye, a direct dye or a lightening dye.

In the case of conventional oxidation dyeing, the fibres are dyed beforehand with at least one oxidation dye, and preferably with at least one oxidation base in the presence of an oxidizing agent.

Thus, in the first compartment of the kit in which it is recommended to use an oxidizing dye such as a standard oxidation dye, at least one oxidation base preferably chosen from para-phenylenediamine and derivatives thereof substituted on one of the amine functions and/or on the benzene nucleus, para-aminophenol and derivatives thereof substituted on the amine functions and/or on the benzene nucleus, double bases, ortho-aminophenols, ortho-phenylenediamines and heterocyclic bases will be present.

Among the heterocyclic bases that may be used as oxidation base according to the invention, mention may be made more particularly of pyridine derivatives, pyrimidine derivatives and pyrazole derivatives. All these compounds may be used in free form or in the form of the addition salts thereof with an acid.

Mention may be made in particular of:
(I) the para-phenylenediamines of formula (I) below, and the addition salts thereof with an acid:

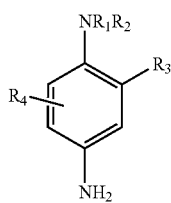

(I)

in which:
R$_1$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous, phenyl or 4'-aminophenyl group;
R$_2$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous group;
R$_3$ represents a hydrogen atom, a halogen atom such as a chlorine atom, a C$_1$–C$_4$ alkyl radical, a sulfo radical, a carboxy radical, a C$_1$–C$_4$ monohydroxyalkyl radical, a C$_1$–C$_4$ hydroxyalkoxy radical, an acetylamino (C$_1$–C$_4$) alkoxy radical, a mesylamino (C$_1$–C$_4$)-alkoxy radical or a carbamoylamino(C$_1$–C$_4$)alkoxy radical,
R$_4$ represents a hydrogen atom, a halogen atom or a C$_1$–C$_4$ alkyl radical;
R$_1$ and R$_2$ may also form, with the nitrogen atom that bears them, a 5- or 6-membered nitrogenous heterocycle optionally substituted with one or more alkyl, hydroxyl or ureido groups;

Among the nitrogenous groups of formula (I) above, mention may be made in particular of amino, mono(C$_1$–C$_4$) alkylamino, di(C$_1$–C$_4$)alkylamino, tri(C$_1$–C$_4$)-alkylamino, monohydroxy(C$_1$–C$_4$)alkylamino, imidazolinium and ammonium radicals.

Among the para-phenylenediamines of formula (I) above, mention may be made more particularly of para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl) -para-phenylenediamine, N-(4-aminophenyl)-para-phenylene-diamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine and 2-methyl-1-N-β-hydroxyethyl-para-phenylenediamine, and the addition salts thereof with an acid.

Among the para-phenylenediamines of formula (I) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

(II) According to the invention, the term double bases is understood to refer to compounds containing at least two aromatic nuclei bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

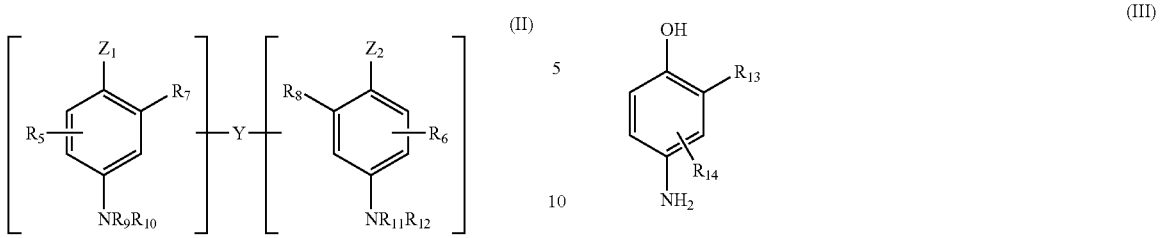

in which:
- $Z_1$ and $Z_2$, which may be identical or different, represent a hydroxyl or —$NH_2$ radical which may be substituted with a $C_1$–$C_4$ alkyl radical or with a linker arm Y;
- the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$–$C_6$ alkoxy radicals;
- $R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
- $R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

it being understood that the compounds of formula (II) contain only one linker arm Y per molecule.

Among the nitrogenous groups of formula (II) above, mention may be made in particular of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazo-linium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-amino-phenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (III) below, and the addition salts thereof with an acid:

in which:
- $R_{13}$ represents a hydrogen atom, a halogen atom, such as fluorine, or a $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl or hydroxy($C_1$–$C_4$)alkylamino($C_1$–$C_4$)alkyl radical, $R_{14}$ represents a hydrogen atom, a halogen atom, such as fluorine, or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy($C_1$–$C_4$)alkyl radical.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

(IV) The ortho-aminophenols that can be used as oxidation bases in the context of the present invention are chosen in particular from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases which can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol;

3-aminopyrazolo-[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)-amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolyl-propylaminopyrazolo[1,5-a]pyrimidine, and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-iso-propylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylamino-pyrazole and 3,5-diamino-4-(β-hydroxyethyl)amino-1-methylpyrazole, and the addition salts thereof with an acid.

In general, the oxidation bases preferably represent from 0.0005% to 12% by weight approximately relative to the total weight of the composition and even more preferably from 0.005% to 8% by weight approximately relative to this weight.

Even more preferably, the keratin fibers are dyed with at least one oxidation base and at least one coupler in the presence of an oxidizing agent.

Consequently, in the first compartment of the kit in which it is recommended to use a standard oxidation dye, at least one oxidation base and at least one coupler will be present.

Among these couplers, mention may be made especially of meta-aminophenols, meta-phenylene-diamines, meta-diphenols, heterocyclic couplers, for instance indole derivatives, indoline derivatives, naphthalene-based derivatives, sesamol and its derivatives, pyridine derivatives, pyrazolotriazole derivatives and pyrazolones, and the addition salts thereof with an acid.

These couplers are chosen more particularly from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 1-acetoxy-2-methylnaphthalene, 2-methyl-1-naphthol, 6-hydroxyindole, 4-hydroxyindole, 4-hydroxy-N-methylindole, 6-hydroxyindoline, 2,6-dihydroxy-4-methyl-pyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

In general, these couplers preferably represent from 0.0001% to 15% by weight approximately relative to the total weight of the dye composition, and even more preferably from 0.001% to 10% by weight approximately.

In general, the addition salts with an acid of the oxidation bases and couplers are chosen from the hydrochlorides, hydrobromides, sulfates, tartrates, lactates and acetates.

The colorations obtained with the standard oxidation dyes may be varied in shade by adding direct dyes: at least one direct dye may therefore also be introduced into the first compartment of the kit or into another separate compartment.

In the case of a direct dye, the fibers are dyed beforehand with at least one direct dye.

Thus, in the first compartment of the kit in which it is recommended to use a direct dye, at least one direct dye will be present.

The direct dyes that may be used to vary the shades obtained using a standard oxidation dye or to dye the fibers via a direct dyeing process, may be chosen especially from neutral, acidic or cationic nitrobenzene direct dyes, neutral, acidic or cationic azo direct dyes, neutral, acidic, or cationic methine direct dyes, neutral, acidic or cationic quinone and in particular anthraquinone direct dyes, azine direct dyes, triarylmethane direct dyes, indoamine direct dyes and natural direct dyes.

Among the benzenic direct dyes, mention may be made in a nonlimiting manner of the following compounds:

1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene 1-hydroxy-2-chloro-6-ethylamino-4-nitrobenzene
1-hydroxy-2-chloro-6-amino-4-nitrobenzene
1-hydroxy-6-[bis(β-hydroxyethyl)amino]-3-nitrobenzene
1-β-hydroxyethylamino-2-nitrobenzene
1-hydroxy-4-β-hydroxyethylamino-3-nitrobenzene.

Among the azo direct dyes that may be mentioned are the cationic azo dyes described in patent applications WO 95/15144, WO 95/01772 and EP 714 954, the content of which forms an integral part of the invention.

Among the azo direct dyes that may also be mentioned are the following dyes described in the Colour Index International 3rd edition: Disperse Red 17; Acid Yellow 9; Acid Black 1; Basic Red 22; Basic Red 76; Basic Yellow 57; Basic Brown 16; Acid Yellow 36; Acid Orange 7; Acid Red 33; Acid Red 35; Basic Brown 17; Acid Yellow 23; Acid Orange 24; Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the methine direct dyes that may be mentioned more particularly are cationic methine dyes such as Basic Red 14, Basic Yellow 13 and Basic Yellow 29.

Among the quinone direct dyes that may be mentioned are the following dyes:
Disperse Red 15; Solvent Violet 13; Acid Violet 43;
Disperse Violet 1; Disperse Violet 4; Disperse Blue 1;
Disperse Violet 8; Disperse Blue 3; Disperse Red 11;
Acid Blue 62; Disperse Blue 7; Basic Blue 22; Disperse Violet 15; Basic Blue 99, and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-bis(β,γ-dihydroxypropylamino)anthraquinone.

Among the azine direct dyes that may be mentioned are the following compounds such as Basic Blue 17 and Basic Red 2.

Among the triarylmethane direct dyes, mention may be made of the following compounds:
Basic Green 1; Acid Blue 9; Basic Violet 3; Basic Violet 14; Basic Blue 7; Acid Violet 49; Basic Blue 26;
Acid Blue 7.

Among the indoamine direct dyes, mention may be made of the following compounds:
  2-β-hydroxyethylamino-5-[bis(β-4'-hydroxyethyl)-amino]anilino-1,4-benzoquinone;
  2-β-hydroxyethylamino-5-(2'-methoxy-4'-amino)anilino-1,4-benzoquinone;
  3-N(2'-chloro-4'-hydroxy)phenylacetylamino-6-methoxy-1,4-benzoquinoneimine;
  3-N(3'-chloro-4'-methylamino)phenylureido-6-methyl-1,4-benzoquinoneimine;
  3-[4'-N-(ethylcarbamylmethyl)amino]phenylureido-6-methyl-1,4-benzoquinoneimine.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

In the case of a lightening dye, the fibers are dyed beforehand with at least one direct dye in the presence of an oxidizing agent.

Thus, in the first compartment of the kit in which it is recommended to use a lightening dye, at least one direct dye will be present.

Among the direct dyes that are preferably used for lightening dyeing, mention may be made of the cationic methine dyes described above, and even more particularly of cationic dyes such as those described in European patent application 1 025 834 by the applicant, which produce very chromatic shades in oxidizing medium.

Said cationic direct dyes preferably used for lightening or non-lightening direct dyeing are especially chosen from those of formula (I) below, and those of formulae (II)a, (II)b, (III)a, (III)b and (IV) to (VII) below, and the mesomeric forms thereof:

(i) dyes of formulae (I), (II)a, (II)b, (III)a and (III)b:

in which formulae (I), (II)a, (II)b, (III)a and (III)b:
$R_1$ represents a hydrogen atom or an amino radical;

R₂ represents a hydrogen atom or a nitro group;

R₃ represents a hydrogen atom, a nitro group or a C₁–C₄ alkoxy radical;

R₄ represents a C₁–C₄ alkyl radical;

R₅ represents a hydrogen atom or a para-tri(C₁–C₄)alkylammoniophenyl group;

R₆ represents a bromine atom or an NH-para-tri(C₁–C₄)alkylammoniophenyl group;

X⁻ represents an anion preferably chosen from chloride, methyl sulfate and acetate;

(ii). dyes of formulae (IV), (V), (VI), (VI') and (VII):

a) the compounds of formula (IV) below:

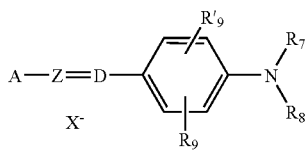

(IV)

in which:

Z and D, which may be identical or different, represent a nitrogen atom or a —CH— radical, R₇ and R₈, which may be identical or different, represent a hydrogen atom; a C₁–C₄ alkyl radical which may be substituted with a —CN, —OH or —NH₂ radical, or form, with a carbon atom of the benzene ring, a heterocycle optionally containing oxygen or nitrogen, which may be substituted with one or more C₁–C₄ alkyl radicals; a 4'-aminophenyl radical, R₉ and R'₉, which may be identical or different, represent a hydrogen atom or a halogen atom chosen from chlorine, bromine, iodine and fluorine, or a cyano, C₁–C₄ alkyl, C₁–C₄ alkoxy or acetyloxy radical, X⁻ represents an anion preferably chosen from chloride, methyl sulfate and acetate;

A represents a group chosen from structures A1 to A19 below:

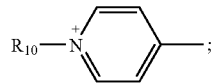

A₁

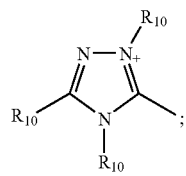

A₂

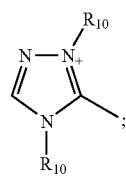

A₃

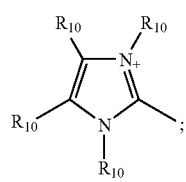

A₄

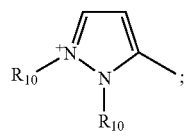

A₅

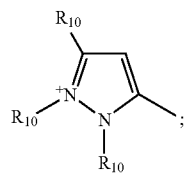

A₆

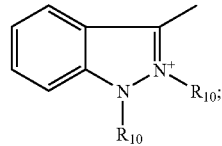

A₇

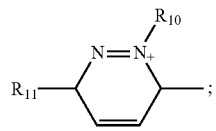

A₈

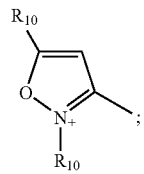

A₉

A₁₀

A₁₁

A₁₂

-continued

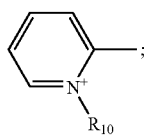  A13

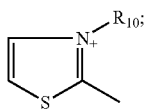  A14

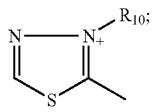  A15

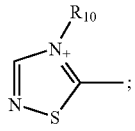  A16

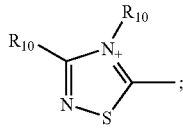  A17

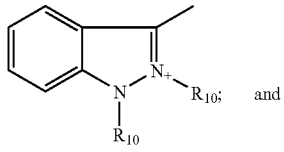  A18

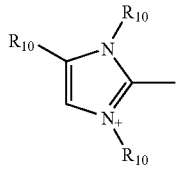  A19

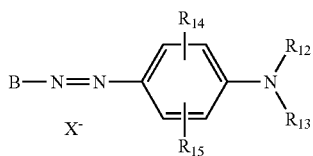

in which $R_{10}$ represents a $C_1$–$C_4$ alkyl radical which may be substituted with a hydroxyl radical and $R_{11}$ represents a $C_1$–$C_4$ alkoxy radical;

b) the compounds of formula (V) below:

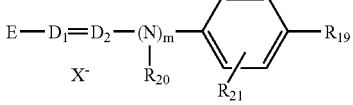  (V)

in which:

$R_{12}$ represents a hydrogen atom or a $C_1$–$C_4$ alkyl radical, $R_{13}$ represents a hydrogen atom, an alkyl radical which may be substituted with a —CN radical or with an amino group, a 4'-aminophenyl radical, or forms with $R_{12}$ a heterocycle optionally containing oxygen and/or nitrogen, which may be substituted with a $C_1$–$C_4$ alkyl radical, $R_{14}$ and $R_{15}$, which may be identical or different, represent a hydrogen atom, a halogen atom such as bromine, chlorine, iodine or fluorine, a $C_1$–$C_4$ alkyl or $C_1$–$C_4$ alkoxy radical, or a —CN radical, $X^-$ represents an anion preferably chosen from chloride, methyl sulfate and acetate;

B represents a group chosen from structures B1 to B6 below:

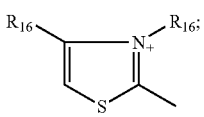  B1

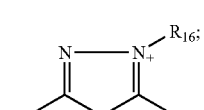  B2

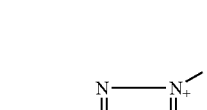  B3

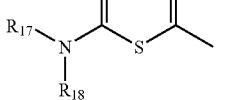  B4

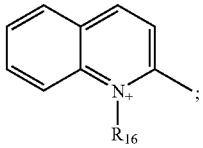  B5

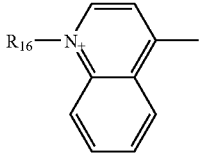  and

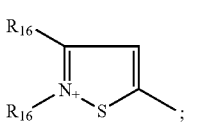  B6 in which $R_{16}$ represents a $C_1$–$C_4$ alkyl radical, $R_{17}$ and $R_{18}$, which may be identical or different, represent a hydrogen atom or a $C_1$–$C_4$ alkyl radical;

c) the compounds of formulae (VI) and (VI') below:

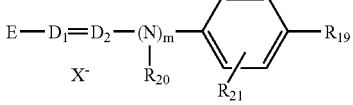  (VI)

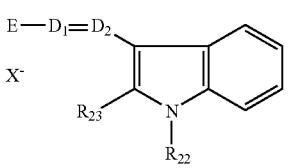  (VI')

in which:

$R_{19}$ represents a hydrogen atom, a $C_1$–$C_4$ alkoxy radical, a halogen atom such as bromine, chlorine, iodine or fluorine, or an amino radical, $R_{20}$ represents a hydrogen atom, a $C_1$–$C_4$ alkyl radical or forms, with a carbon atom of the benzene ring, a heterocycle optionally containing oxygen and/or substituted with one or more $C_1$–$C_4$ alkyl groups, $R_{21}$ represents a hydrogen atom or a halogen atom such as bromine, chlorine, iodine or fluorine, $R_{22}$ and $R_{23}$, which may be identical or different, represent a hydrogen atom or a $C_1$–$C_4$ alkyl radical, $D_1$ and $D_2$, which may be identical or different, represent a nitrogen atom or a —CH group, m=0 or 1, $X^-$ represents an anion preferably chosen from chloride, methyl sulfate and acetate, E represents a group chosen from structures E1 to E8 below:

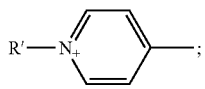
E1

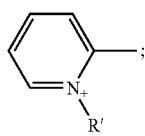
E2

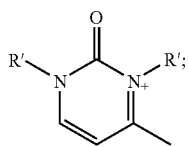
E3

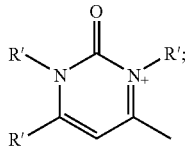
E4

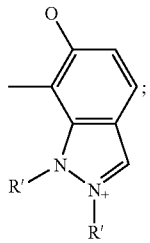
E5

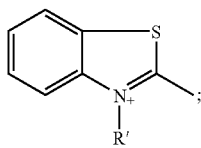
E6

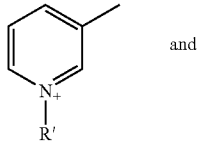
E7 and

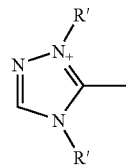
E8 in which R' represents a $C_1$–$C_4$ alkyl radical;

when m=0 and $D_{13}$ represents a nitrogen atom, then E may also denote a group of structure E9 below:

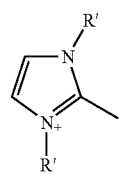
E9 in which R' represents a $C_1$–$C_4$ alkyl radical;

d) the compounds of formula (VII) below:

$$G-N=N-J \qquad (VII)$$

in which:

the symbol G represents a group chosen from the structures $G_1$ to $G_3$ below:

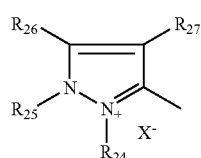
$G_1$

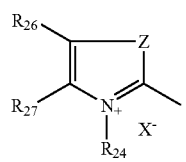
$G_2$

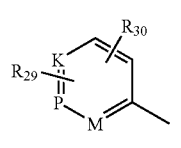
$G_3$ in which structures $G_1$ to $G_3$, $R_{24}$ denotes a $C_1$–$C_4$ alkyl radical, a phenyl radical which may be substituted with a $C_1$–$C_4$ alkyl radical, or a halogen atom chosen from chlorine, bromine, iodine and fluorine;

$R_{25}$ denotes a $C_1$–$C_4$ alkyl radical or a phenyl radical;

$R_{26}$ and $R_{27}$, which may be identical or different, represent a $C_1$–$C_4$ alkyl radical, a phenyl radical, or form together in $G_1$ a benzene ring substituted with one or more $C_1$–$C_4$ alkyl, $C_1$–$C_4$ alkoxy or $NO_2$ radicals, or form together in G$_2$ a benzene ring optionally substituted with one or more C$_1$–C$_4$ alkyl, C$_1$–C$_4$ alkoxy or NO$_2$ radicals;

R$_{26}$ may also denote a hydrogen atom;

Z denotes an oxygen or sulfur atom or a group —NR$_{25}$;

M represents a group —CH, —CR (R denoting C$_1$–C$_4$ alkyl) or

—NR$_{28}$(X$^-$)$_r$;

K represents a group —CH, —CR (R denoting C$_1$–C$_4$ alkyl) or

—NR$_{28}$(X$^-$)$_r$;

P represents a group —CH, —CR (R denoting C$_1$–C$_4$ alkyl) or

—NR$_{28}$(X$^-$)$_r$;

r denotes 0 or 1;

R$_{28}$ represents an O$^-$ atom, a C$_1$–C$_4$ alkoxy radical or a C$_1$–C$_4$ alkyl radical;

R$_{29}$ and R$_{30}$, which may be identical or different, represent a hydrogen atom or a halogen atom chosen from chlorine, bromine, iodine and fluorine, a C$_1$–C$_4$ alkyl or C$_1$–C$_4$ alkoxy radical, or an —NO$_2$ radical;

X$^-$ represents an anion preferably chosen from chloride, iodide, methyl sulfate, ethyl sulfate, acetate and perchlorate;

the symbol J represents:

(a) a group of structure J$_1$ below:

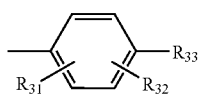

in which structure J$_1$,

R$_{31}$ represents a hydrogen atom, a halogen atom chosen from chlorine, bromine, iodine and fluorine, a C$_1$–C$_4$ alkyl or C$_1$–C$_4$ alkoxy radical, an —OH, —NO$_2$, —NHR$_{34}$, —NR$_{35}$R$_{36}$ or C$_1$–C$_4$ —NHCOalkyl radical, or forms with R$_{32}$ a 5- or 6-membered ring optionally containing one or more hetero atoms chosen from nitrogen, oxygen and sulfur;

R$_{32}$ represents a hydrogen atom, a halogen atom chosen from chlorine, bromine, iodine and fluorine, a C$_1$–C$_4$ alkyl or C$_1$–C$_4$ alkoxy radical, or forms with R$_{33}$ or R$_{34}$ a 5- or 6-membered ring optionally containing one or more hetero atoms chosen from nitrogen, oxygen and sulfur;

R$_{33}$ represents a hydrogen atom, an —OH radical, a radical —NHR$_{34}$ or a radical —NR$_{35}$R$_{36}$;

R$_{34}$ represents a hydrogen atom, a C$_1$–C$_4$ alkyl radical, a C$_1$–C$_4$ monohydroxyalkyl or C$_2$–C$_4$ polyhydroxyalkyl radical or a phenyl radical;

R$_{35}$ and R$_{36}$, which may be identical or different, represent a C$_1$–C$_4$ alkyl radical or a C$_1$–C$_4$ monohydroxyalkyl or C$_2$–C$_4$ polyhydroxyalkyl radical;

(b) a 5- or 6-membered nitrogenous heterocyclic group, which may contain other hetero atoms and/or carbonyl groups and may be substituted with one or more C$_1$–C$_4$ alkyl, amino or phenyl radicals, and especially a group of structure J$_2$ below:

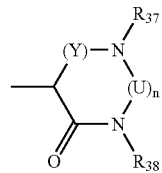

in which structure J$_2$,

R$_{37}$ and R$_{38}$, which may be identical or different, represent a hydrogen atom, a C$_{13}$–C$_{10}$ alkyl radical or a phenyl radical;

Y denotes a —CO— radical or a

radical;

N=0 or 1, with, when n denotes 1, U denotes a —CO— radical.

Among the cationic direct dyes of formula (IV), mention may be made more particularly of the compounds corresponding to structures (IV1) to (IV54) below:

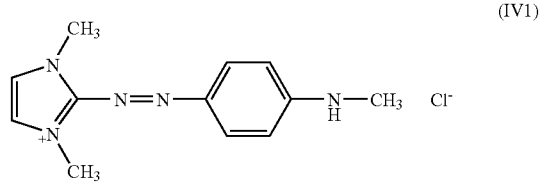
(IV1)

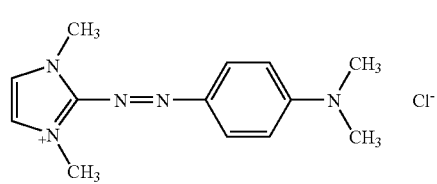
(IV2)

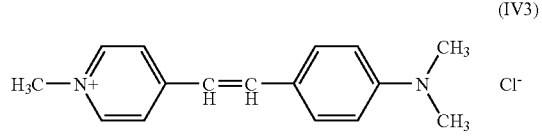
(IV3)

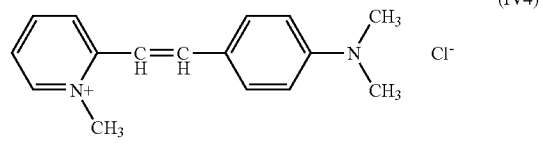
(IV4)

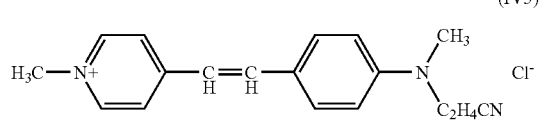
(IV5)

-continued
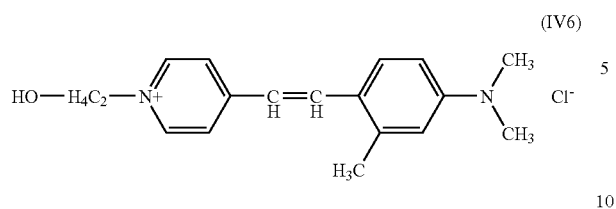
(IV6)
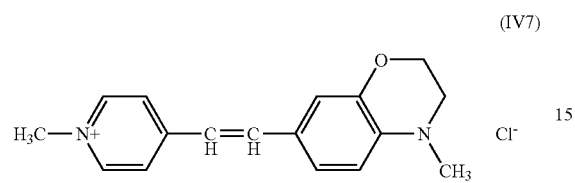
(IV7)
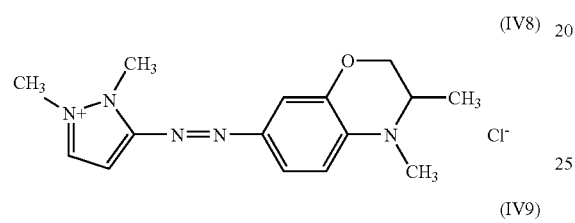
(IV8)
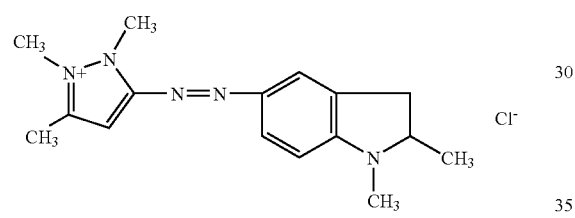
(IV9)
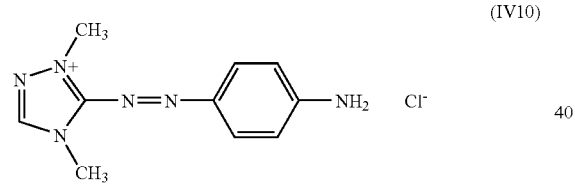
(IV10)
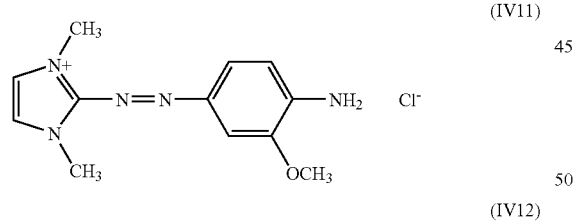
(IV11)
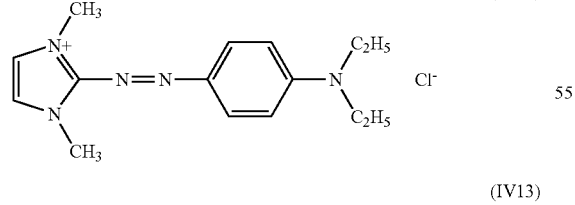
(IV12)
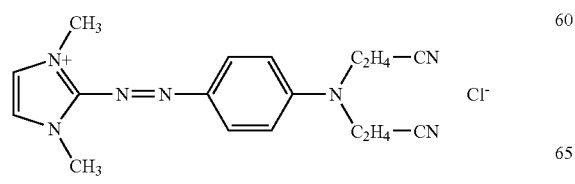
(IV13)
-continued
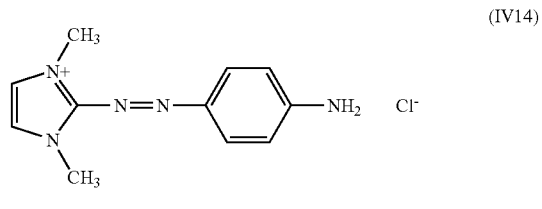
(IV14)
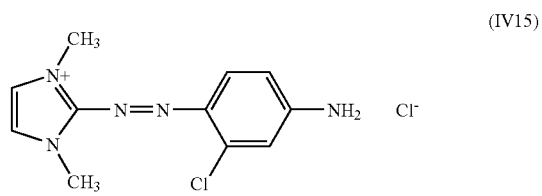
(IV15)
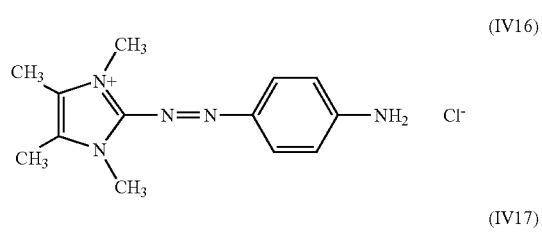
(IV16)
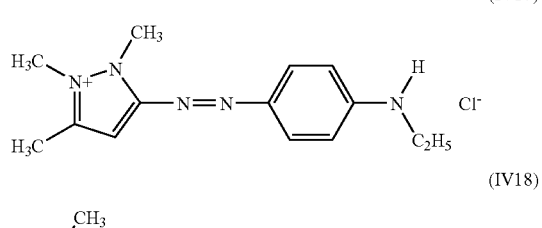
(IV17)
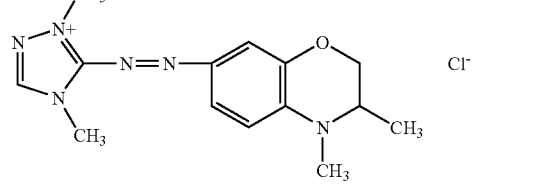
(IV18)
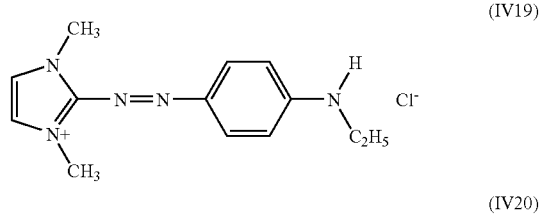
(IV19)
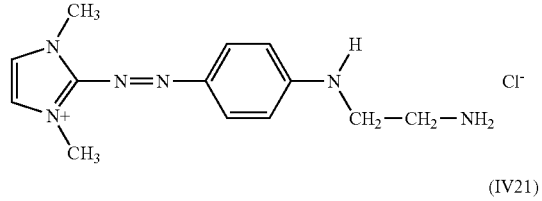
(IV20)
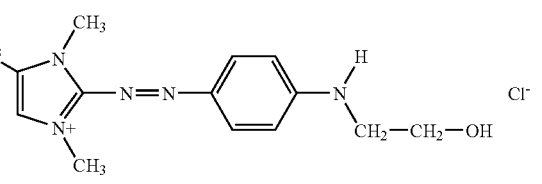
(IV21)

(IV22)
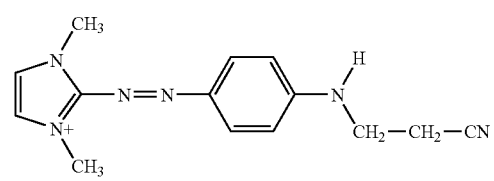
(IV23)
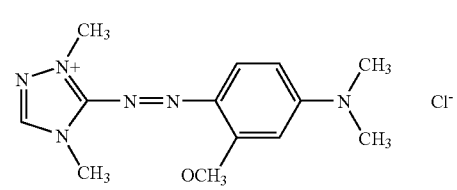
(IV24)
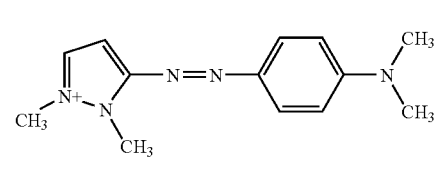
(IV25)
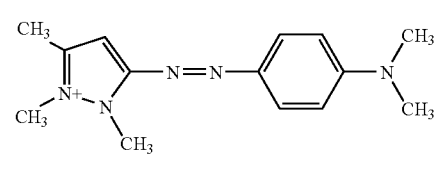
(IV26)
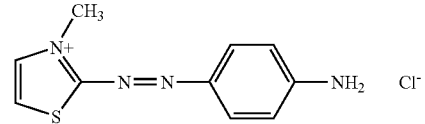
(IV27)
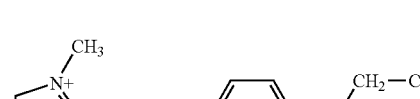
(IV28)
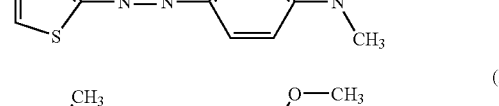
(IV29)
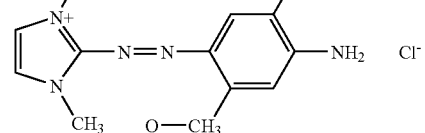
(IV30)
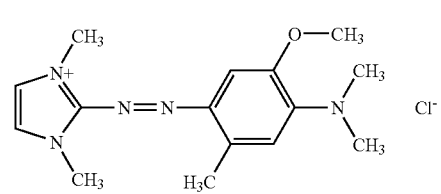
(IV31)
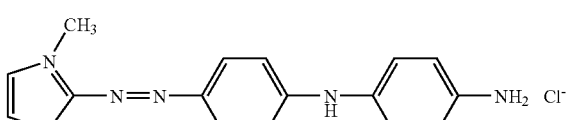
(IV32)
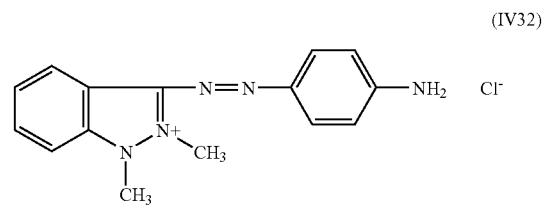
(IV33)
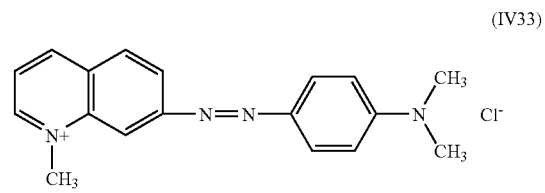
(IV34)
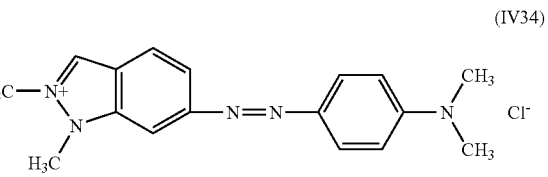
(IV35)
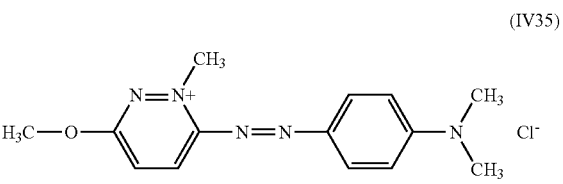
(IV36)
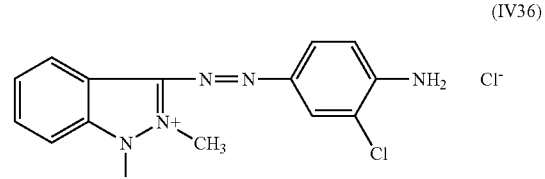
(IV37)
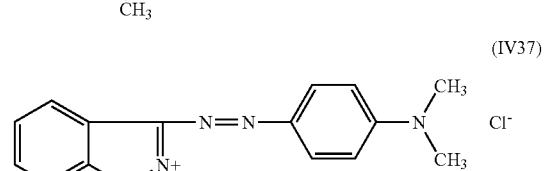
(IV38)
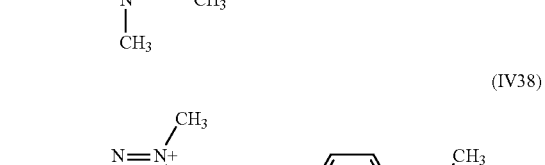

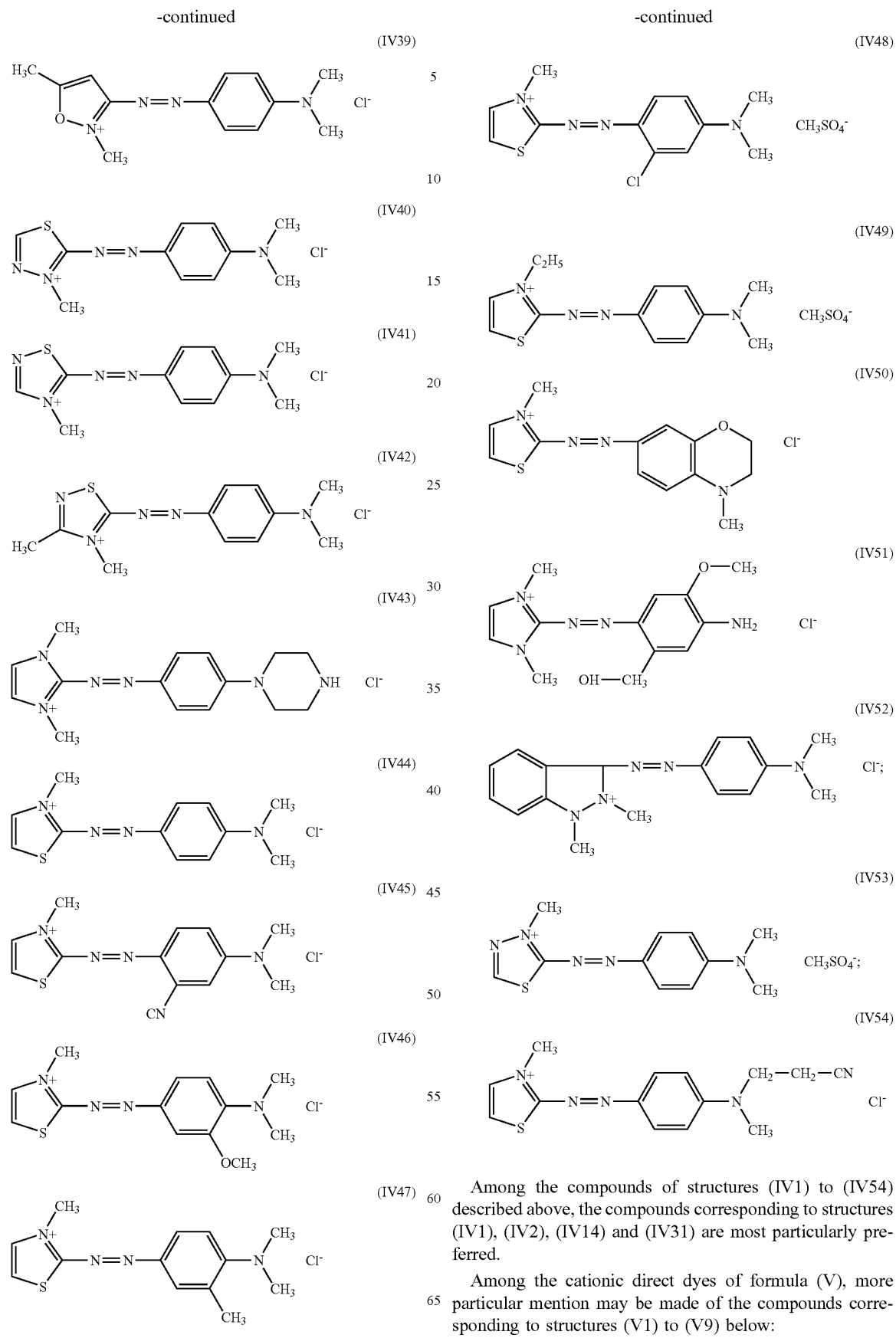
Among the compounds of structures (IV1) to (IV54) described above, the compounds corresponding to structures (IV1), (IV2), (IV14) and (IV31) are most particularly preferred.
Among the cationic direct dyes of formula (V), more particular mention may be made of the compounds corresponding to structures (V1) to (V9) below:

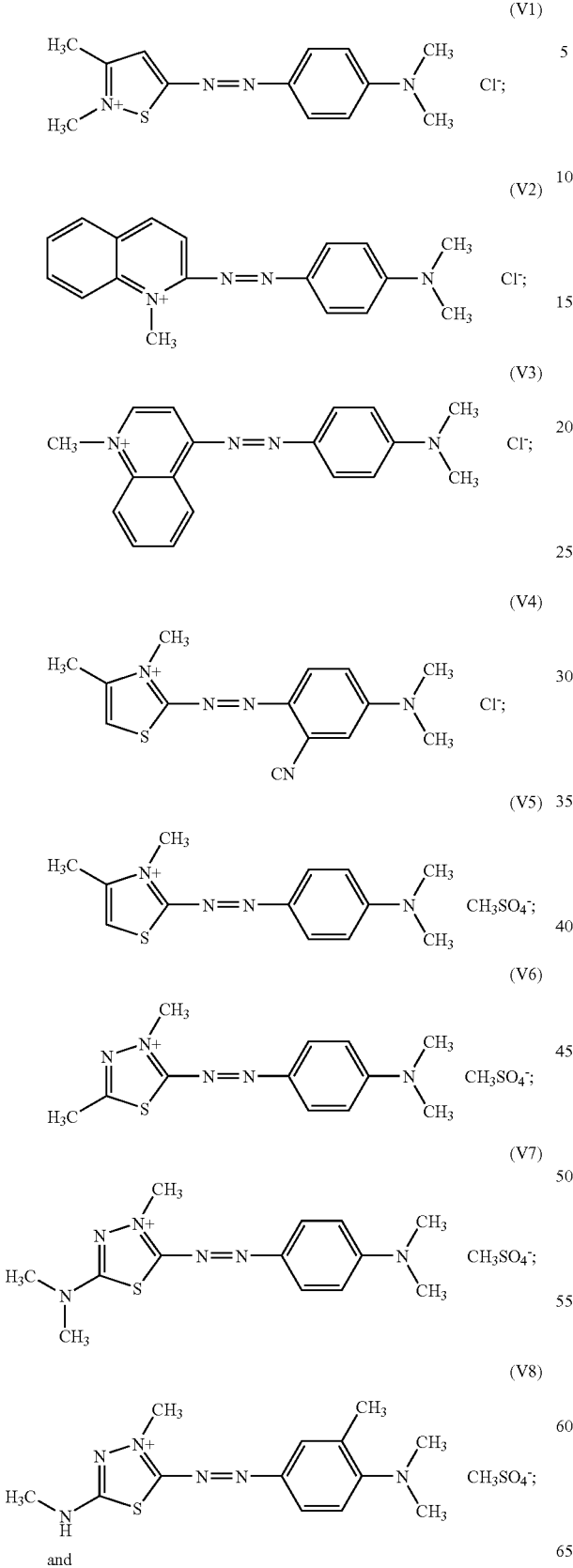
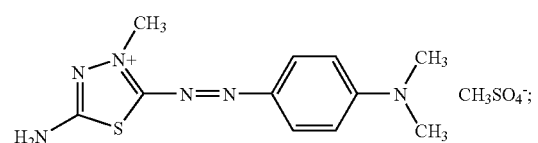
Among the cationic direct dyes of formula (VI) that may be used in the dye compositions in accordance with the invention, mention may be made more particularly of the compounds corresponding to structures (VI1) to (VI18) below:
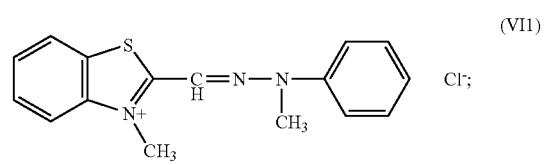
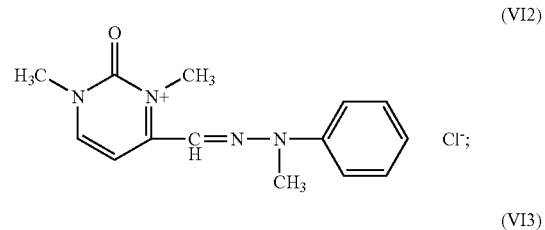
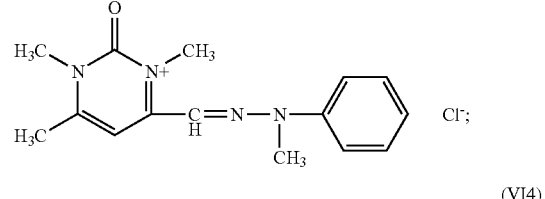
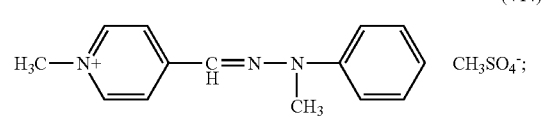
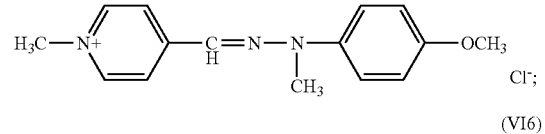
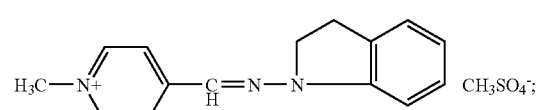
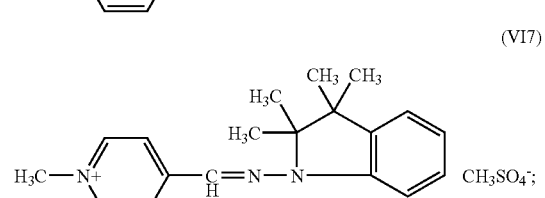

-continued (VI8)
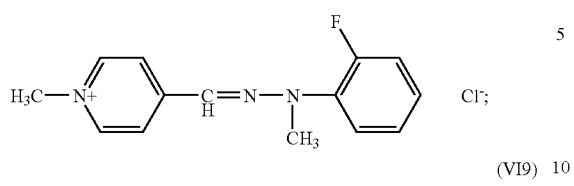

(VI9)
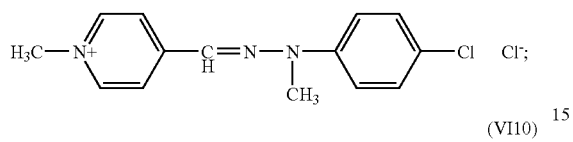

(VI10)
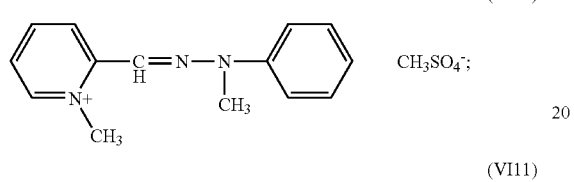

(VI11)
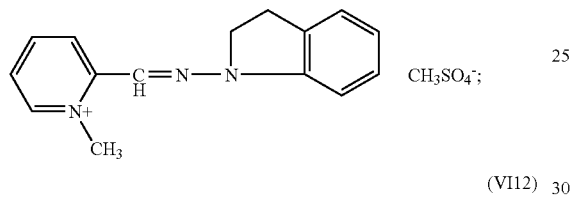

(VI12)
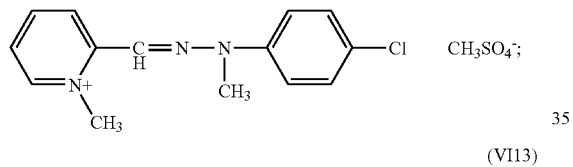

(VI13)
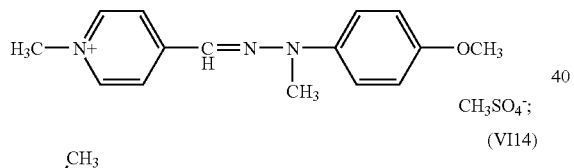

(VI14)
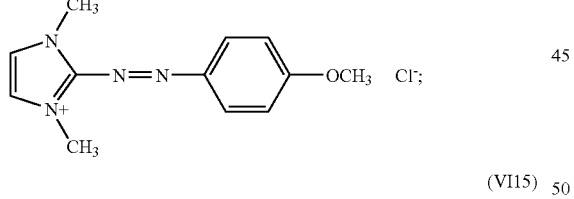

(VI15)
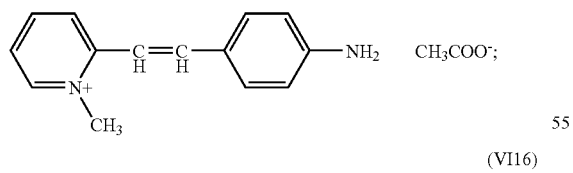

(VI16)
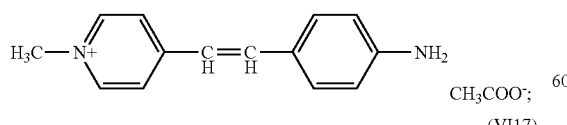

(VI17)
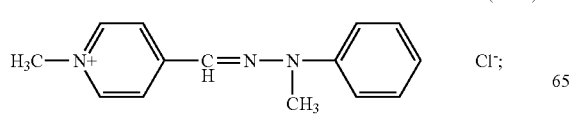

-continued (VI18)
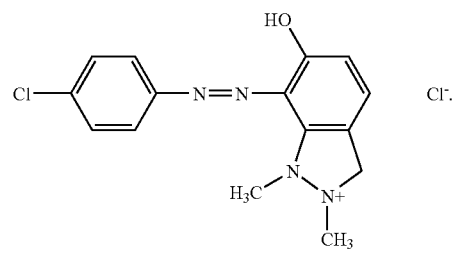

Among the particular compounds of structures (VI1) to (VI18) described above, the ones most particularly preferred are the compounds corresponding to structures (VI4), (VI5) and (VI13).

Among the cationic direct dyes of formula (VI') that may be mentioned more particularly are the compounds corresponding to structures (VI'1) to (VI'3) below:

(VI'1)
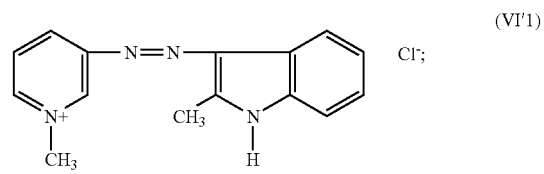

(VI'2)
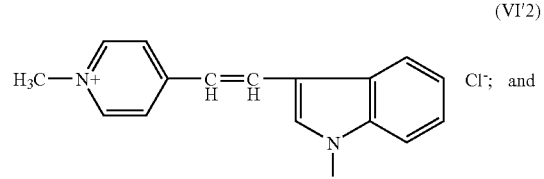

(VI'3)
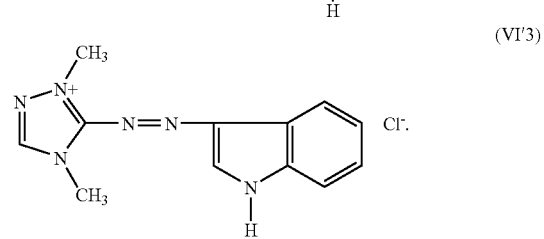

Among the cationic direct dyes of formula (VII) that may be mentioned more particularly are the compounds of structures (VII$_1$) to (VII$_{77}$) below:

(VII1)
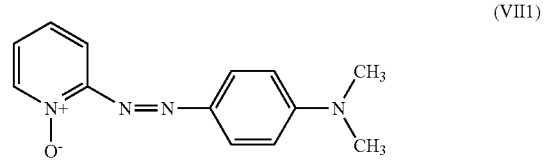

(VII2)
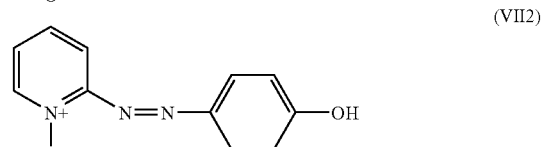

-continued
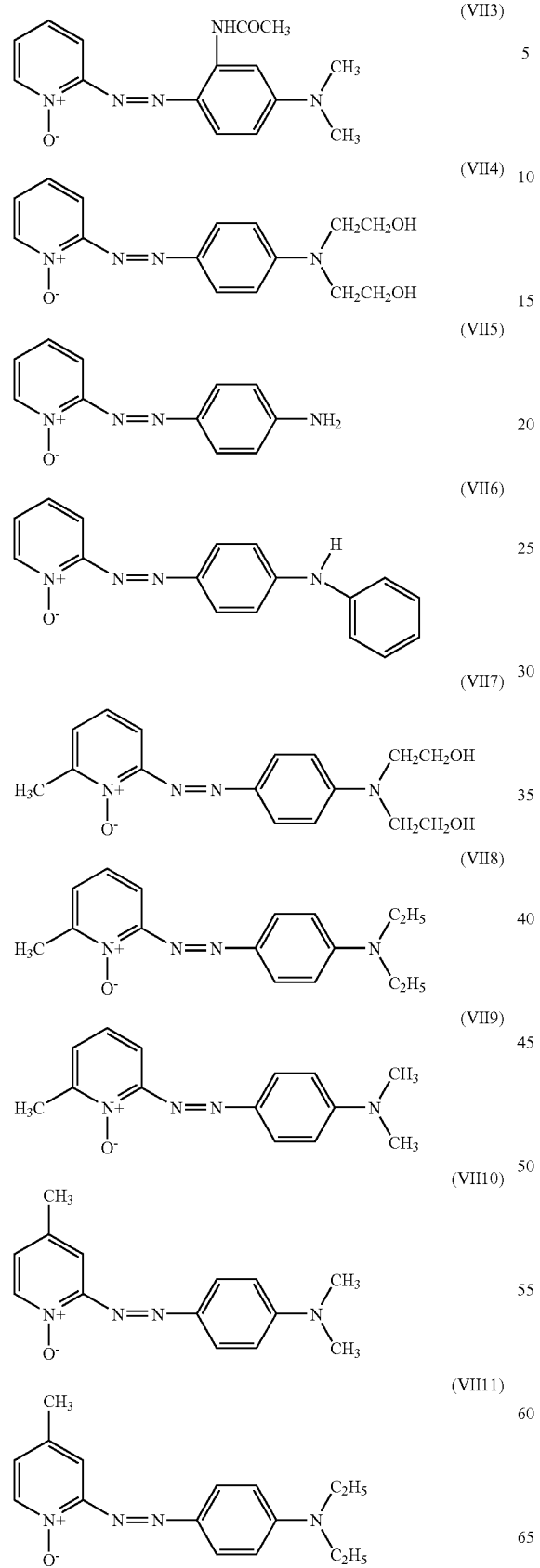
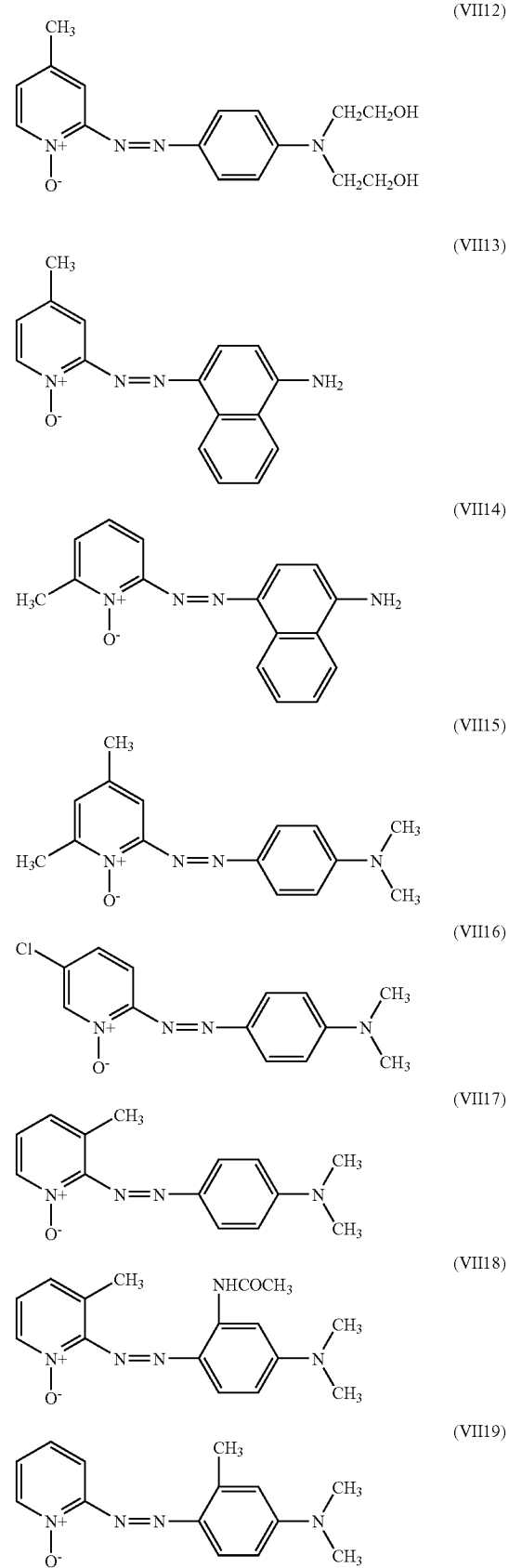

-continued (VII20) (VII29) (VII21) (VII30) (VII22) (VII31) (VII23) (VII32) (VII24) (VII33) (VII25) (VII34) (VII26) (VII35) (VII27) (VII36) (VII28)

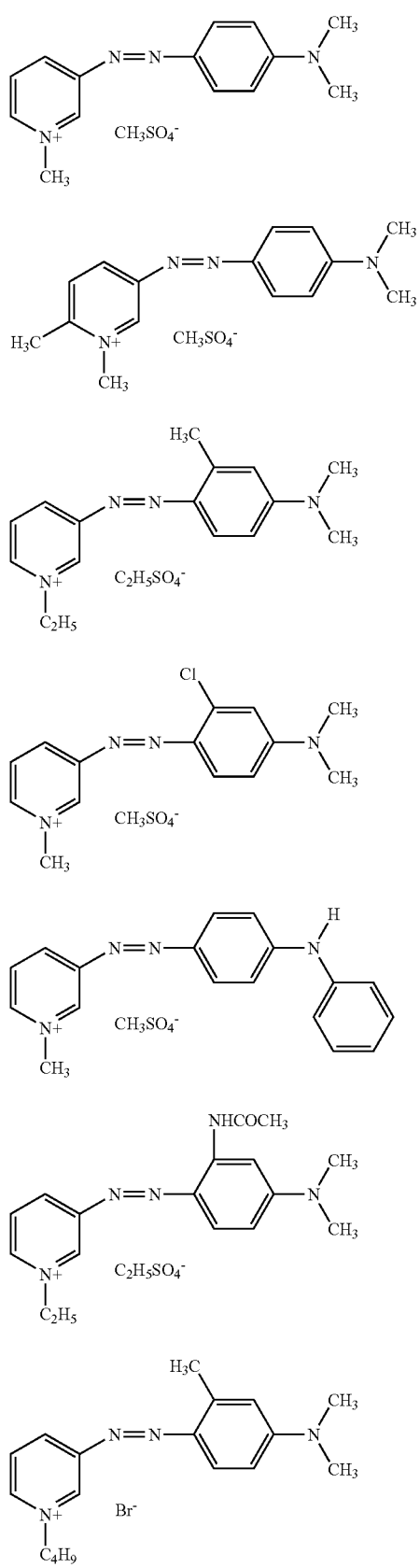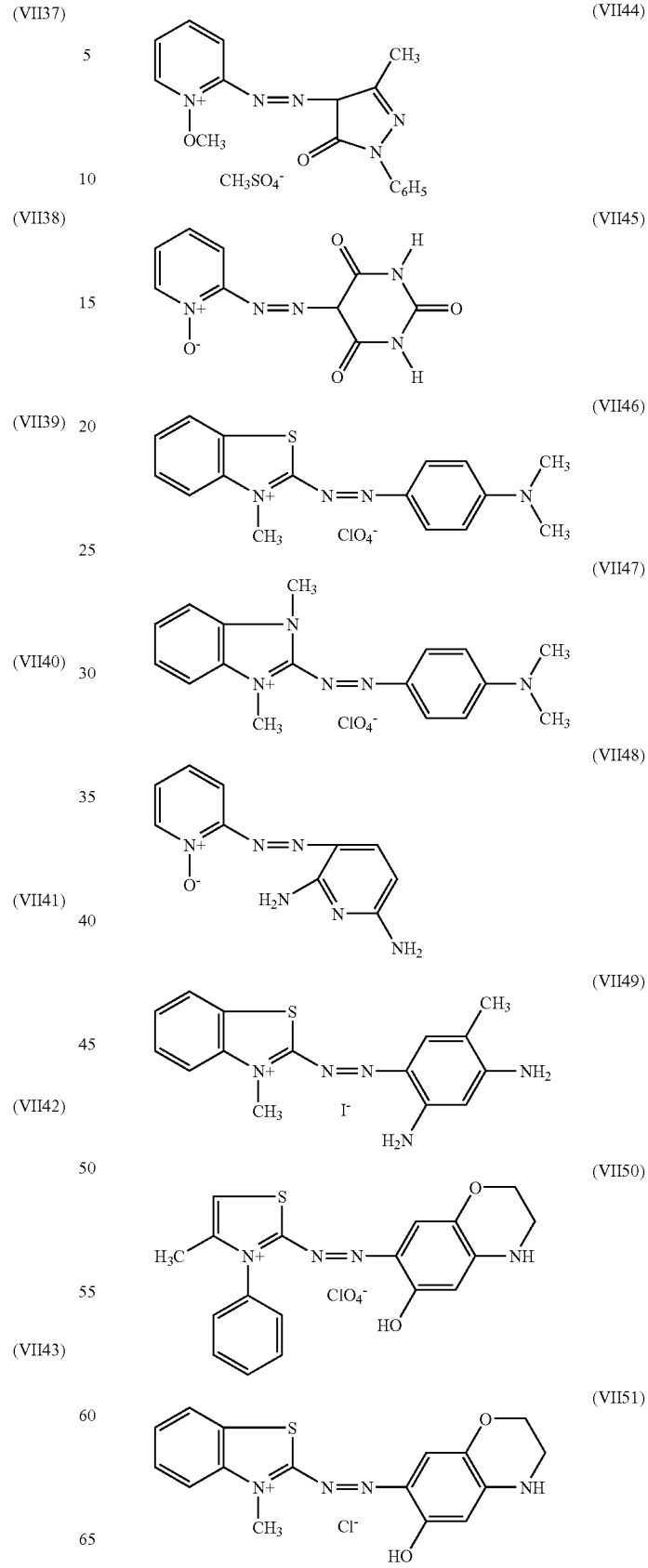

-continued
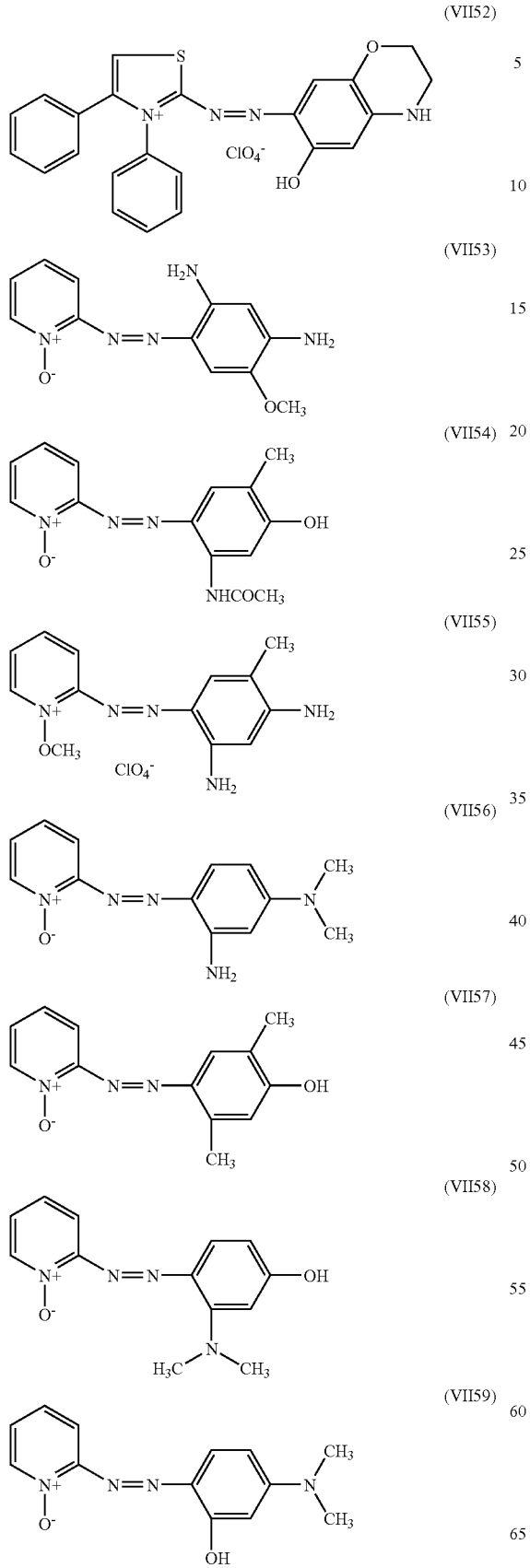
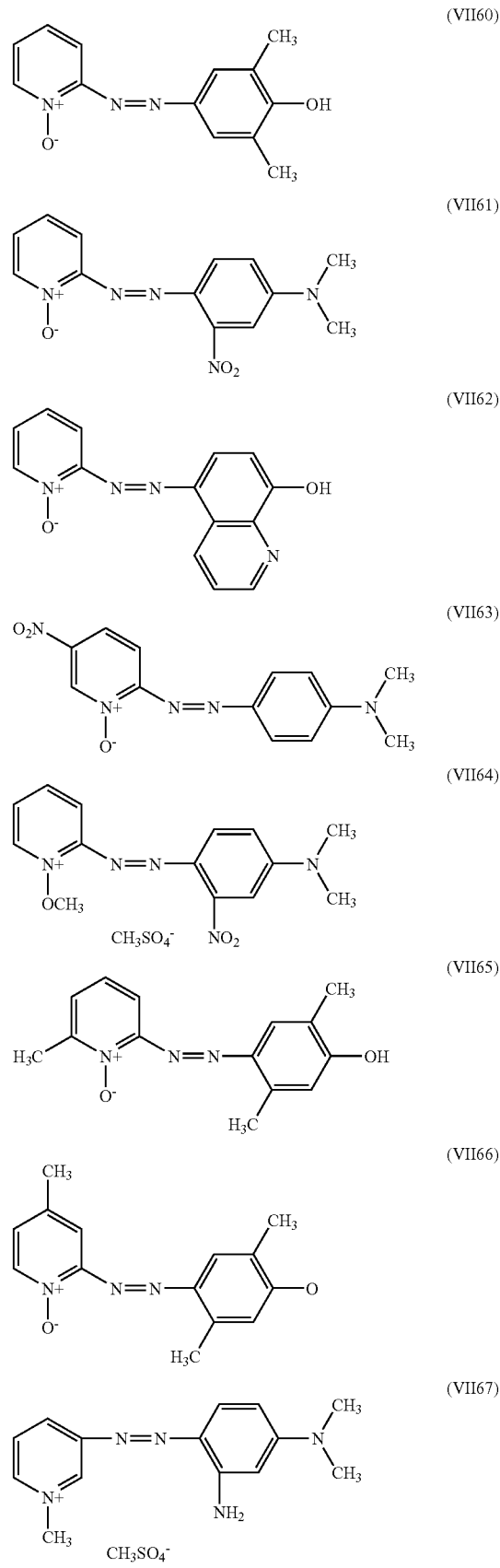

-continued (VII68) 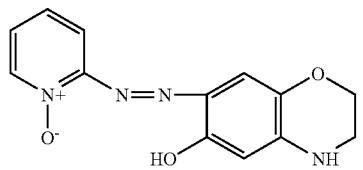

(VII69) 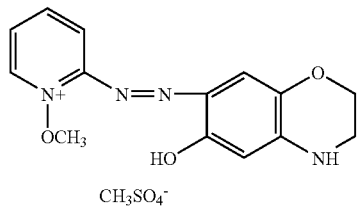

(VII70) 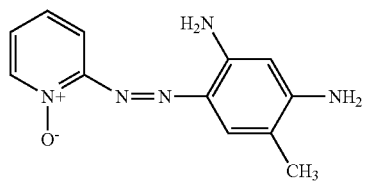

(VII71) 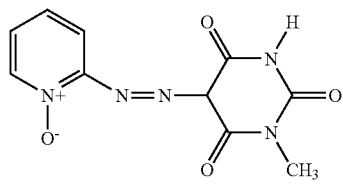

(VII72) 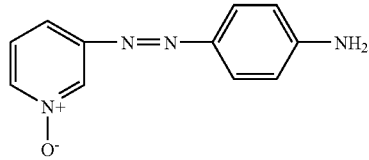

(VII73) 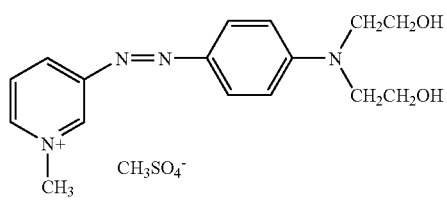

(VII74) 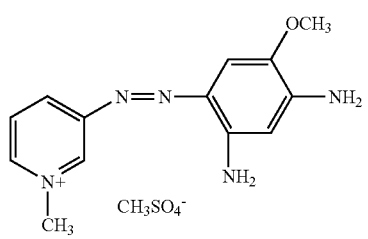

(VII75) 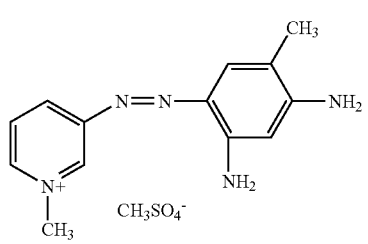

-continued (VII76) 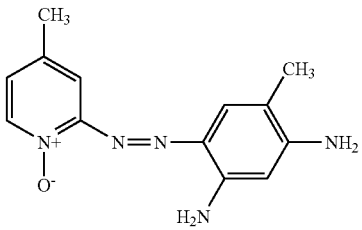

(VII77) 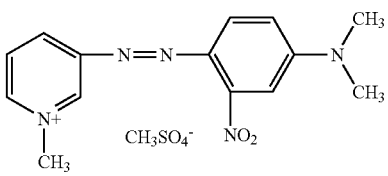

All these particularly fast dyes of formulae (I) to (VII) can be stripped using the bleaching composition according to the present invention and most particularly the dyes of formulae (IV2) (=Basic Red 51), (IV14) (=Basic Orange 31) and (VI4) (=Basic Yellow 87).

The direct dye(s) preferably represent(s) from 0.001% to 20% by weight approximately and even more preferably from 0.005% to 10% by weight approximately relative to the total weight of the oxidizing or non-oxidizing dye composition.

In the multi-compartment kit, the oxidizing agent required to perform the oxidation dyeing or the lightening dyeing operation is separate from the oxidation dye(s) or from the cationic direct dye(s). It is preferably chosen from hydrogen peroxide, urea peroxide, alkali metal bromates or ferricyanides, and persalts such as perborates and persulfates, the use of hydrogen peroxide being particularly preferred. This oxidizing agent advantageously consists of an aqueous hydrogen peroxide solution whose titer can range more particularly from about 1 to 40 volumes and even more preferably from about 5 to 40 volumes.

It is also possible to use as oxidizing agent one or more redox enzymes such as 4-electron oxidoreductases (such as laccases), and 2-electron oxidoreductases (such as uricase), where appropriate in the presence of the respective donor or co-factor thereof.

The cosmetically acceptable medium that is suitable for bleaching (or the support for the composition), in accordance with the invention, generally consists of water or of a mixture of water and of at least one organic solvent to dissolve the compounds that would not be sufficiently water-soluble. Examples of organic solvents that may be mentioned include $C_1$–$C_4$ alkanols, such as ethanol and isopropanol; glycerol; glycols and glycol ethers, for instance 2-butoxyethanol, propylene glycol, dipropylene glycol, hexylene glycol, propylene glycol monomethyl ether, diethylene glycol monoethyl ether and monomethyl ether, and also aromatic alcohols, for instance benzyl alcohol or phenoxyethanol, similar products and mixtures thereof.

Said solvents may then be present in proportions preferably of between 0.5% and 20% and more particularly from 2% to 10% by weight relative to the total weight of the bleaching composition.

The pH of the bleaching composition in accordance with the invention is preferably between 1.8 and 6.

It is adjusted with acidifying or basifying agents, in amounts ranging from 0.01% to 30% by weight relative to the total weight of the composition.

Among the acidifying agents that may be mentioned, for example, are mineral or organic acids, for instance etidronic acid, hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkaline carbonates, alkanolamines, such as monoethanolamine, diethanolamine and triethanolamine, 2-methyl-2-amino-1-propanol and derivatives thereof, sodium hydroxide, potassium hydroxide and the compounds of formula (III) below:

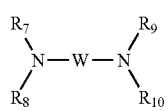

(III)

in which W represents a propylene residue optionally substituted with a hydroxyl group or a $C_1$–$C_4$ alkyl radical; $R_7$, $R_8$, $R_9$ and $R_{10}$, which may be identical or different, represent a hydrogen atom or a $C_1$–$C_4$ alkyl or $C_1$–$C_4$ hydroxyalkyl radical.

The bleaching composition according to the invention may also contain reducing agents other than those of formula (I) according to the invention, chosen especially from α-oxocarboxylic acids such as oxalic acid, glyoxalic acid, pyruvic acid or α-ketoglutaric acid.

The bleaching composition in accordance with the invention may contain at least one thickener in a proportion of between 0.01% and 10% and in particular between 0.1% and 5% by weight approximately relative to the total weight of the composition.

They are preferably chosen from cellulose derivatives, guar derivatives, gums of microbial or plant origin and synthetic thickeners.

Thickeners:

Among the cellulose derivatives that may be mentioned are hydroxy($C_1$–$C_6$)alkylcelluloses and carboxy ($C_1$–$C_6$) alkylcelluloses.

The hydroxy($C_1$–$C_6$)alkylcelluloses are more particularly hydroxyethylcelluloses, such as those sold under the names Cellosize QP3L, Cellosize QP4400H, Cellosize QP30000H, Cellosize HEC30000A and Cellosize Polymer PCG10 by the company Amerchol, or Natrosol 250HHR, Natrosol 250MR, Natrosol 250M, Natrosol 250HHXR, Natrosol 250HHX, Natrosol 250HR and Natrosol HX by the company Hercules, or Tylose H1000 by the company Hoechst.

The hydroxy($C_1$–$C_6$)alkylcelluloses are also, more particularly, hydroxypropylcelluloses such as the products sold under the names Klucel EF, Klucel H, Klucel LHF, Klucel MF and Klucel G by the company Aqualon.

Among the carboxy($C_1$–$C_6$)alkylcelluloses preferably used is carboxymethylcellulose, for which mention may be made of the products sold under the names Blanose 7M8/SF, Blanose Raffinée 7M, Blanose 7LF, Blanose 7MF, Blanose 9M31F, Blanose 12M31XP, Blanose 12M31P, Blanose 9M31XF, Blanose 7H, Blanose 7M31 and Blanose 7H3SXF by the company Aqualon, or Aquasorb A500 and Ambergum 1221 by the company Hercules, or Cellogen HP810A and Cellogen HP6HS9 by the company Montello, or Primellose by the company Avebe.

Among the guar derivatives, mention may be made of modified or unmodified nonionic guar gums. The unmodified guar gums are, for example, the products sold under the name Vidogum GH 175 by the company Unipectine and under the names Meypro-Guar 50 and Jaguar C by the company Meyhall. The modified nonionic guar gums are especially modified with $C_1$–$C_6$ hydroxyalkyl groups. Among the hydroxyalkyl groups that may be mentioned, for example, are hydroxymethyl, hydroxyethyl, hydroxypropyl and hydroxybutyl groups.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhône-Poulenc (Meyhall) or under the name Galactasol 4H4FD2 by the company Aqualon.

Among the gums of microbial origin, mention may be made of biopolysaccharide gums such as scleroglucans or xanthans.

The scleroglucans are represented for example by the products sold under the name Actigum CS by the company Sanofi Bio Industries and in particular Actigum CS 11, and under the name Amigel by the company Alban Muller International. Other scleroglucans, such as the one treated with glyoxal in French patent application No. 2 633 940, can also be used.

The xanthans are represented, for example, by the products sold under the names Keltrol, Keltrol T, Keltrof TF, Keltrol BT, Keltrol RD and Keltrol CG by the company Nutrasweet Kelco, or under the names Rhodicare S and Rhodicare H by the company Rhodia Chimie.

Among the gums of plant origin, mention may be made of those derived from plant exudates, such as gum arabic, ghatti gum, karaya gum, gum tragacanth, carrageenan, agar and carob gum.

Pectins, alginates and starches may also be used.

All these compounds are well known to those skilled in the art and are described in particular in the book by Robert L. Davidson entitled "Handbook of Water soluble gums and resins" published by McGraw Hill Book Company (1980).

Synthetic Thickeners:

Among these are amphiphilic polymers, also known as "associative polymers", comprising at least one fatty chain, and of anionic, nonionic, cationic or amphoteric type.

Amphiphilic or "Associative" Polymers:

Among the polymers comprising at least one fatty chain and of anionic type, mention may be made of:

(I) those comprising at least one hydrophilic unit and at least one fatty-chain allyl ether, more particularly those in which the hydrophilic unit consists of an ethylenic unsaturated anionic monomer, even more particularly of a vinylcarboxylic acid and most particularly an acrylic acid, a methacrylic acid or mixtures thereof, the fatty-chain allyl ether unit corresponding to the monomer of formula (XV) below:

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (XV) that is more particularly preferred is a unit in which R' denotes H, n is equal to 10 and R denotes a stearyl ($C_{18}$) radical.

Anionic amphiphilic polymers of this type are described and prepared, according to an emulsion polymerization process, in patent EP-0 216 479.

Among these fatty-chain anionic thickening polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (XV), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80 and Salcare SC 90, which are aqueous 30% emulsions of a crosslinked terpolymer of methacrylic acid, of ethyl acrylate and of steareth-10 allyl ether (40/50/10).

(II) those comprising at least one hydrophilic unit of olefinic unsaturated carboxylic acid type, and at least one hydrophobic unit of unsaturated carboxylic acid ($C_{10}$–$C_{30}$) alkyl ester type.

Preferably, these polymers are chosen from those in which the hydrophilic unit of unsaturated olefinic carboxylic acid type corresponds to the monomer of formula (XVI) below:

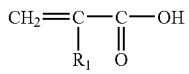

(XVI)

in which $R_1$ denotes H or $CH_3$ or $C_2H_5$, i.e. acrylic acid, methacrylic acid or ethacrylic acid units, and in which the hydrophobic unit of the type such as a ($C_{10}$–$C_{30}$) alkyl ester of an unsaturated carboxylic acid corresponds to the monomer of formula (XVII) below:

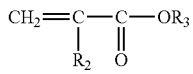

(XVII)

in which formula $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$–$C_{30}$ and preferably $C_{12}$–$C_{22}$ alkyl radical.

($C_{10}$–$C_{30}$)Alkyl esters of unsaturated carboxylic acids in accordance with the invention comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic polymers of this type are disclosed and prepared, for example, according to U.S. Pat. Nos. 3,915,921 and 4,509,949.

Among the fatty-chain anionic thickening polymers of this type that will be used more particularly are polymers formed from a mixture of monomers comprising:

(i) essentially acrylic acid,
(ii) an ester of formula (XVI) described above, in which $R_2$ denotes H or $CH_3$, $R_3$ denoting an alkyl radical containing from 12 to 22 carbon atoms,
(iii) a crosslinking agent, which is a well-known copolymerizable polyethylenic unsaturated monomer, for instance diallyl phthalate, allyl (meth)acrylate, divinylbenzene, (poly)ethylene glycol dimethacrylate or methylenebisacrylamide.

Among the fatty-chain anionic thickening polymers of this type that will be used more particularly are those consisting of from 95% to 60% by weight of acrylic acid (hydrophilic unit), 4% to 40% by weight of $C_{10}$–$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$–$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1, Pemulen TR2 and Carbopol 1382, and even more preferentially Pemulen TR1, and the product sold by the company SEPPIC under the name Coatex SX.

(III) maleic anhydride/$C_{30}$–$C_{38}$ α-olefin/alkyl maleate terpolymers, such as the product (maleic anhydride/$C_{30}$–$C_{38}$ α-olefin/isopropyl maleate copolymer) sold under the name Performa V 1608 by the company Newphase Technologies.

(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$–$C_4$ alcohol.

An example of a compound of this type that may be mentioned is Aculyn 22 sold by the company Rohm & Haas, which is a methacrylic acid/ethyl acrylate/stearyl methacrylate oxyalkylenated terpolymer.

Among the fatty-chain polymers of nonionic type that are preferably chosen are:
  (1) celluloses modified with groups comprising at least one fatty chain; examples that may be mentioned include:
    hydroxyethylcelluloses modified with groups comprising at least one fatty chain, such as alkyl, arylalkyl or alkylaryl groups, or mixtures thereof, and in which the alkyl groups are preferably $C_8$–$C_{22}$, for instance the product Natrosol Plus Grade 330 CS ($C_{16}$ alkyls) sold by the company Aqualon, or the product Bermocoll EHM 100 sold by the company Berol Nobel, those modified with alkylphenyl polyalkylene glycol ether groups, such as the product Amercell Polymer HM-1500 (nonylphenyl polyethylene glycol (15) ether) sold by the company Amerchol.
  (2) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc.
  (3) copolymers of vinylpyrrolidone and of fatty-chain hydrophobic monomers; examples that may be mentioned include:
    the products Antaron V216 or Ganex V216 (vinylpyrrolidone/hexadecene copolymer) sold by the company I.S.P.
    the products Antaron V220 or Ganex V220 (vinylpyrrolidone/eicosene copolymer) sold by the company I.S.P.
  (4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208.
  (5) copolymers of hydrophilic methacrylates or acrylates and of hydrophobic monomers comprising at least one fatty chain, such as, for example, the polyethylene glycol methacrylate/lauryl methacrylate copolymer.
  (6) polyurethane polyethers comprising in their chain both hydrophilic blocks usually of polyoxyethylenated nature and hydrophobic blocks which may be aliphatic sequences alone and/or cycloaliphatic and/or aromatic sequences.
  (7) polymers with an aminoplast ether skeleton containing at least one fatty chain, such as the Pure Thix compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1 000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205 containing a urea function, sold by the company Rheox, or Rheolate 208, 204 or 212, and also Acrysol RM 184, Aculyn 44 and Aculyn 46, from the company Rohm & Haas [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis (4-cyclohexylisocyanate) (SMDI), at 35% by weight in a mixture of propylene glycol (39%) and water (26%)].

Mention may also be made of the product Elfacos T210 containing a $C_{12-14}$ alkyl chain, and the product Elfacos T212 containing a $C_{18}$ alkyl chain, from Akzo.

The product DW 1206B from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate 255, Rheolate 278 and Rheolate 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Among the fatty-chain polymers of cationic type that may be mentioned are the quaternized cellulose derivatives, which are, in particular:
  quaternized celluloses modified with groups comprising at least one fatty chain, such as alkyl, arylalkyl or alkylaryl groups containing at least 8 carbon atoms, or mixtures thereof.
  quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethyl-celluloses containing $C_8$–$C_{30}$ fatty chains that may be mentioned include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

The quaternized or nonquaternized polyacrylates containing amino side groups contain, for example, hydrophobic groups of the steareth-20 type (polyoxyethylenated (20) stearyl alcohol).

Examples of polyacrylates containing amino side chains that may be mentioned include the polymers 8781-121B or 9492-103 sold by the company National Starch.

Among the polymers comprising at least one fatty chain and of amphoteric type that are preferably chosen are those comprising at least one noncyclic cationic unit. Even more particularly, the ones that are preferred are those prepared from or comprising 1 to 20 mol %, preferably 1.5 to 15 mol % and even more particularly 1.5 to 6 mol % of fatty-chain monomer relative to the total number of moles of monomers.

The fatty-chain amphoteric polymers that are preferred according to the invention comprise or are prepared by copolymerizing:

1) at least one monomer of formula (Ia) or (Ib):

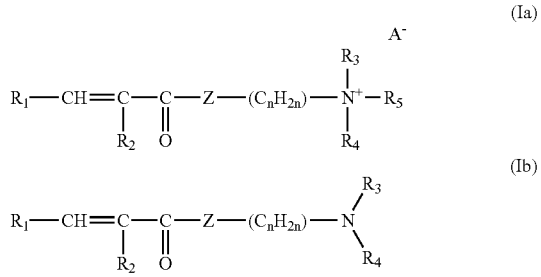

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom,
n is an integer from 2 to 5,
$A^-$ is an anion derived from an organic or mineral acid, such as a methosulfate anion or a halide such as chloride or bromide;

2) at least one monomer of formula (II)

$$R_6\text{---}CH\text{=}CR_7\text{---}COOH \quad (II)$$

in which $R_6$ and $R_7$, which may be identical or different, represent a hydrogen atom or a methyl radical; and 3) at least one monomer of formula (III):

$$R_6\text{---}CH\text{=}CR_7\text{---}COXR_8 \quad (III)$$

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) of the present invention are preferably chosen from the group consisting of:
- dimethylaminoethyl methacrylate, dimethylaminoethyl acrylate,
- diethylaminoethyl methacrylate, diethylaminoethyl acrylate,
- dimethylaminopropyl methacrylate, dimethylaminopropyl acrylate,
- dimethylaminopropylmethacrylamide, dimethylaminopropylacrylamide, these monomers optionally being quaternized, for example with a $C_1$–$C_4$ alkyl halide or a $C_1$–$C_4$ dialkyl sulfate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from the group consisting of acrylic acid, methacrylic acid, crotonic acid and 2-methylcrotonic acid. More particularly, the monomer of formula (II) is acrylic acid.

The monomers of formula (III) of the present invention are preferably chosen from the group consisting of $C_{12}$–$C_{22}$ and more particularly $C_{16}$–$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The fatty-chain amphoteric polymers according to the invention preferably comprise from 1 mol % to 10 mol % of the monomer comprising a fatty chain (monomer of formula (Ia), (Ib) or (III)), and preferably from 1.5 mol % to 6 mol %.

The weight-average molecular weights of the fatty-chain amphoteric polymers according to the invention may range from 500 to 50 000 000 and are preferably between 10 000 and 5 000 000.

The fatty-chain amphoteric polymers according to the invention may also contain other monomers such as nonionic monomers and in particular such as $C_1$–$C_4$ alkyl acrylates or methacrylates.

Fatty-chain amphoteric polymers according to the invention are described and prepared, for example, in patent application WO 98/44012.

Among the fatty-chain amphoteric polymers according to the invention, the ones that are preferred are acrylic acid/(meth)acrylamidopropyltrimethyl-ammonium chloride/stearyl methacrylate copolymers.

The bleaching composition in accordance with the invention may also contain various adjuvants conventionally used in hair-bleaching compositions.

Adjuvants:

Among these adjuvants, surfactants may be present and may be chosen, without preference, alone or as mixtures, from anionic, amphoteric, nonionic, zwitterionic and cationic surfactants.

The surfactants that are suitable for carrying out the present invention are especially the following:

(i) Anionic Surfactant(s):

By way of example of anionic surfactants that can be used, alone or as mixtures, in the context of the present invention, mention may be made in particular (nonlimiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$–$C_{24}$) alkyl sulfosuccinates, ($C_6$–$C_{24}$)alkyl ether sulfosuccinates, ($C_6$–$C_{24}$)alkylamide sulfosuccinates; ($C_6$–$C_{24}$)alkyl sulfoacetates; ($C_6$–$C_{24}$)acyl sarcosinates; and ($C_6$–$C_{24}$)acyl glutamates. It is also possible to use ($C_6$–$C_{24}$)alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated $(C_6–C_{24})$alkyl ether carboxylic acids, polyoxyalkylenated $(C_6–C_{24})$alkylaryl ether carboxylic acids, polyoxyalkylenated $(C_6–C_{24})$ alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178) and their nature is not a critical factor in the context of the present invention. Thus, they can be chosen in particular from (nonlimiting list) polyethoxylated or polypropoxylated, alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}–C_{14})$alkylamine oxides or N-acylaminopropylmorpholine oxides.

(iii) Amphoteric or Zwitterionic Surfactant(s):

The amphoteric or zwitterionic surfactants, the nature of which is not a critical factor in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of $(C_8–C_{20})$alkylbetaines, sulfobetaines, $(C_8–C_{20})$ alkylamido$(C_1–C_6)$alkylbetaines or $(C_8–C_{20})$alkylamido $(C_1–C_6)$alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

$R_{34}$—CONHCH$_2$CH$_2$—N($R_{35}$) ($R_{36}$) (CH$_2$COO$^-$) in which: $R_{34}$ denotes an alkyl radical of an acid $R_{34}$—COOH present in hydrolyzed coconut oil, a heptyl, nonyl or undecyl radical, $R_{35}$ denotes a beta-hydroxyethyl group and $R_{36}$ denotes a carboxymethyl group; and $R_{34}'$—CONHCH$_2$CH$_2$—N(B) (C)

in which:

B represents —CH$_2$CH$_2$OX', C represents —(CH$_2$)$_z$—Y', with z=1 or 2,

X' denotes the —CH$_2$CH$_2$—COOH group or a hydrogen atom,

Y' denotes —COOH or the —CH$_2$—CHOH—SO$_3$H radical, $R_{34}'$ denotes an alkyl radical of an acid $R_{37}$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

(iv) Cationic Surfactants:

Among the cationic surfactants, mention may be made in particular (nonlimiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the ready-to-use composition according to the invention can range from 0.01% to 40% and preferably from 0.1% to 30% relative to the total weight of the composition.

Other adjuvants may also be present, and among these are nonionic, anionic, amphoteric, zwitterionic and cationic conditioning polymers, or mixtures thereof, and preferably cationic or amphoteric substantive polymers.

The substantive nature (i.e. the ability to be deposited on the hair) of the polymers used in accordance with the invention is conventionally determined by means of the test described by Richard J. Crawford, Journal of the Society of Cosmetic Chemists, 1980, 31 (5), pages 273 to 278 (development with the dye Acidic Red 80).

Cationic Substantive Polymers:

For the purposes of the present invention, the term "cationic polymer" denotes any polymer containing cationic groups and/or groups that may be ionized into cationic groups.

The cationic polymers that may be used in accordance with the present invention may be chosen from all those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and 5×10$^6$ approximately and preferably between 10$^3$ and 3×10$^6$ approximately.

Among the cationic polymers that may be mentioned more particularly are polymers of the polyamine, polyamino amide and polyquaternary ammonium type.

These are known products. They are described in particular in French patents Nos 2 505 348 and 2 542 997. Among said polymers, mention may be made of:

(1) Homopolymers or copolymers derived from acrylic or methacrylic esters or amides and comprising at least one of the units of formula (I), (II), (III) or (IV) below:

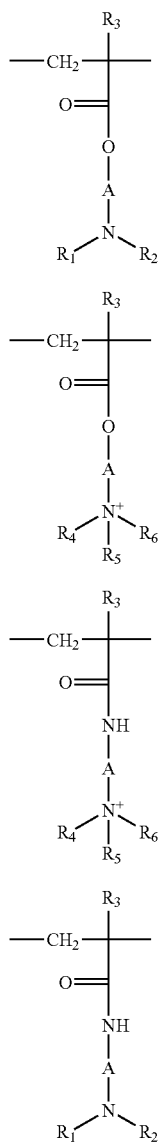

in which:

$R_3$, which may be identical or different, denote a hydrogen atom or a $CH_3$ radical;

A, which may be identical or different, represent a linear or branched alkyl group containing 1 to 6 carbon atoms, preferably 2 or 3 carbon atoms, or a hydroxyalkyl group containing 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or nonquaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcapro-lactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives containing quaternary ammonium groups, described in French patent 1 492 597, and in particular polymers sold under the name "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyl-diallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 and Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylamino-hydroxypropyl/diethylenetriamine polymers sold under the name Cartaretine F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

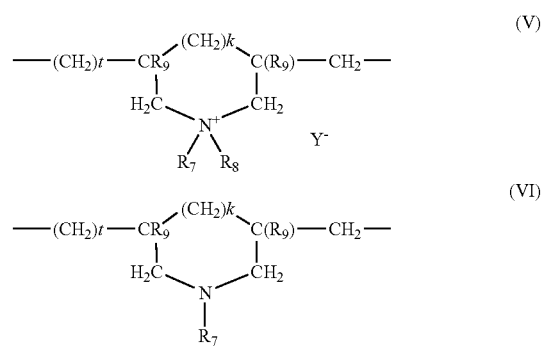

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 22 carbon atoms, a hydroxyalkyl group in which the alkyl group preferably has 1 to 5 carbon atoms, a lower ($C_1$–$C_4$) amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group containing from 1 to 4 carbon atoms; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallyl-ammonium chloride homopolymer sold under the name Merquat 100 by the company Calgon (and its homologs of low weight-average molecular mass) and the copolymers of diallyldimethylammonium chloride and of acrylamide sold under the name Merquat 550.

(10) The quaternary diammonium polymer containing repeating units corresponding to the formula:

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and
X⁻ denotes an anion derived from a mineral or organic acid;
A1, $R_{10}$ and $R_{12}$ can form, with the two nitrogen atoms to which they are attached, a piperazine ring; in addition, if A1 denotes a linear or branched, saturated or unsaturated alkylene or hydroxyalkylene radical, B1 can also denote a group —$(CH_2)_n$—CO—D—OC—$(CH_2)_n$— in which D denotes:

a) a glycol residue of formula: —O—Z—O—, where Z denotes a linear or branched hydrocarbon-based radical or a group corresponding to one of the following formulae:

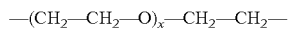

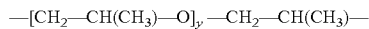

where x and y denote an integer from 1 to 4, representing a defined and unique degree of polymerization or any number from 1 to 4 representing an average degree of polymerization;

b) a bis-secondary diamine residue such as a piperazine derivative;
c) a bis-primary diamine residue of formula: —NH—Y—NH—, where Y denotes a linear or branched hydrocarbon-based radical, or alternatively the divalent radical

—$CH_2$—$CH_2$—S—S—$CH_2$—$CH_2$—;

d) a ureylene group of formula: —NH—CO—NH—.

Preferably, X⁻ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to formula (VIII) below:

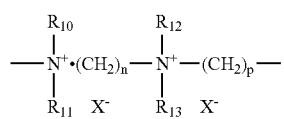

(VIII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X⁻ is an anion derived from a mineral or organic acid.

(11) Polyquaternary ammonium polymers consisting of repeating units of formula (IX):

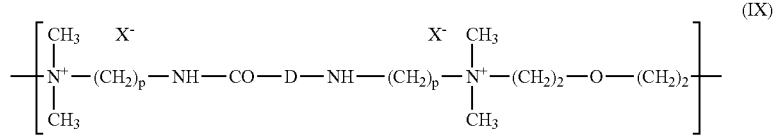

(IX)

in which p denotes an integer ranging from 1 to 6 approximately, D may be nothing or may represent a group —$(CH_2)_r$—CO— in which r denotes a number equal to 4 or 7, and X⁻ is an anion.

Such polymers may be prepared according to the processes described in U.S. Pat. Nos. 4,157,388, 4,702,906 and 4,719,282. They are especially described in patent application EP-A-122 324.

Among these products, mention may be made, for example, of Mirapol A 15, Mirapol AD1, Mirapol AZ1 and Mirapol 175 sold by the company Miranol.

(12) Quaternary polymers of vinylpyrrolidone and of vinylimidazole, such as, for example, the products sold under the names Luviquat FC 905, FC 550 and FC 370 by the company BASF.

(13) Polyamines such as Polyquart H sold by Henkel, which is given under the reference name "Polyethylene glycol (15) tallow polyamine" in the CTFA dictionary.

(14) Crosslinked methacryloyloxy($C_1$–$C_4$)alkyltri ($C_1$–$C_4$)-alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of said copolymer in mineral oil can be used more particularly. This dispersion is sold under the name Salcare® SC 92 by the company Allied Colloids. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Allied Colloids.

Other cationic polymers that can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use the polymers of families (1), (9), (10), (11) and (14) and even more preferably the polymers containing repeating units of formulae (W) and (U) below:

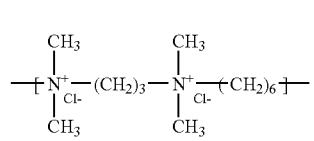

(W)

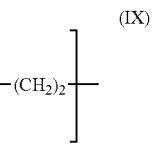

and in particular those whose molecular weight, determined by gel permeation chromatography, is between 9500 and 9900;

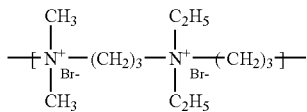
(U)

and especially those whose molecular weight, determined by gel permeation chromatography, is about 1200.

The concentration of cationic substantive polymer in the composition according to the present invention may range from 0.01% to 10%, preferably from 0.05% to 5% and even more preferably from 0.1% to 3% by weight relative to the total weight of the composition.

Amphoteric Substantive Polymers:

The amphoteric polymers that may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer sold under the name Polyquart KE 3033 by the company Henkel.

The vinyl compound may also be a dialkyldiallylammonium salt such as dimethyldiallyl-ammonium chloride. The copolymers of acrylic acid and of the latter monomer are sold under the names Merquat 280, Merquat 295 and Merquat Plus 3330 by the company Calgon.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacryl-amide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) crosslinked and alkylated polyamino amides partially or totally derived from polyamino amides of general formula:

(X)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

(XI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

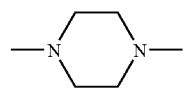

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) polymers containing zwitterionic units of formula:

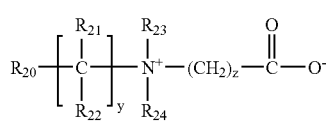
(XII)

in which $R_{20}$ denotes a polymerizable unsaturated group such as an acrylate, methacrylate, acrylamide or methacrylamide group, y and z represent an integer from 1 to 3, $R_{21}$, and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethylcarboxymethyl-ammonioethyl methacrylate such as the product sold under the name Diaformer Z301 by the company Sandoz.

(5) polymers derived from chitosan, comprising monomer units corresponding to formulae (XIII), (XIV) and (XV) below:

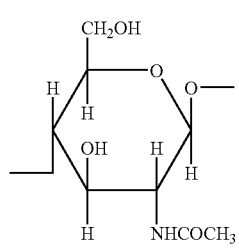
(XIII)

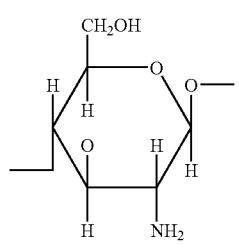
(XIV)

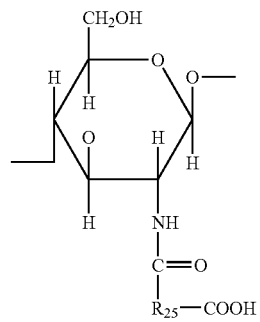
(XV)

the unit (XIII) being present in proportions of between 0 and 30%, the unit (XIV) in proportions of between 5% and 50% and the unit (XV) in proportions of between 30% and 90%, it being understood that, in this unit (XV), $R_{25}$ represents a radical of formula:

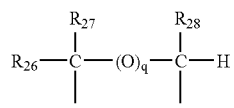

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom; or, if q=1, $R_{26}$, $R_{27}$ and $R_{28}$ each represent a hydrogen atom, and also the salts formed by these compounds with bases or acids.

(6) polymers derived from the N-carboxyalkylation of chitosan, such as N-carboxymethylchitosan or N-carboxybutylchitosan sold under the name "Evalsan" by the company Jan Dekker.

(7) polymers corresponding to the general formula (XI) as described, for example, in French patent 1 400 366:

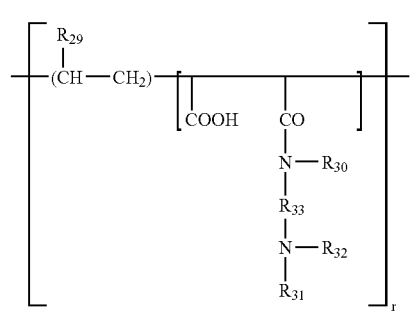
(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—N($R_{31}$)$_2$, $R_{33}$ representing a —CH$_2$—CH$_2$—, —CH$_2$—CH$_2$—CH$_2$— or —CH$_2$—CH(CH$_3$)— group, $R_{31}$ having the meanings mentioned above, and also the higher homologs of these radicals and containing up to 6 carbon atoms, r is such that the molecular weight is between 500 and 6 000 000 and preferably between 1000 and 1 000 000;

(8) amphoteric polymers of the type —D—X—D—X— chosen from:
 a) polymers obtained by the action of chloroacetic acid or sodium chloroacetate on compounds containing at least one unit of formula:

—D—X—D—X—D— (XVII)

where D denotes a radical

and X denotes the symbol E or E', E or E+, which may be identical or different, denote a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

—D—X—D—X— (XVIII)

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C$_1$–C$_5$)alkyl vinyl ether/maleic anhydride copolymers partially modified by semiamidation with an N,N-dialkylaminoalkylamine such as N,N-dimethylamino-propylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric substantive polymer(s) may represent from 0.01% to 10% by weight, preferably from 0.05% to 5% by weight and even more preferably from 0.1% to 3% by weight relative to the total weight of the composition.

Other adjuvants, such as penetrating agents, sequestering agents, fragrances, dispersants, volatile or nonvolatile, modified or unmodified silicones, film-forming agents, ceramides, preserving agents, opacifiers, mineral or plant oils, waxes and vitamins, may also be present in the bleaching composition according to the invention.

Needless to say, a person skilled in the art will take care to select this or these optional additional compound(s) such that the advantageous properties intrinsically associated with the bleaching composition in accordance with the invention are not, or are not substantially, adversely affected by the envisaged addition(s).

The composition in accordance with the invention may be in various forms, such as in the form of solutions, emulsions, creams, gels, optionally pressurized in the form of mousses, or in any other form that is suitable for bleaching human keratin fibers, and especially the hair.

It may be obtained by extemporaneous mixing, at the time of use, either:

(a) of an anhydrous composition containing at least one sulfinic acid derivative of formula (I) as defined above, or a salt thereof, and of an aqueous composition at acidic pH, or (b) of two aqueous compositions, one of which contains at least one sulfinic acid derivative of formula (I) as defined above, or a salt thereof, at acidic or alkaline pH, and the other contains an aqueous composition at acidic pH.

Preferably, according to the present invention, the composition for bleaching at a pH of between 1.5 and 9 and preferably between 1.8 and 6 is obtained by extemporaneous mixing, at the time of use, of two aqueous compositions, one of which contains at least one sulfinic acid derivative of formula (I) as defined above, or a salt thereof, at acidic or alkaline pH, and the other contains an aqueous composition at acidic pH.

In this case and preferably, the aqueous composition at acidic pH is in the form of a gel or an emulsion and may contain a fragrance, the emulsion containing at least one oil or a fatty substance and at least one water-soluble emulsifier.

According to the bleaching process, at least one bleaching composition as defined above is applied to the dyed fibers, at an application temperature of between room temperature and 80° C., for a time that is sufficient to partially or totally degrade the coloration arising from the oxidation dyeing or non-oxidation dyeing of the keratin fibers. Preferably, the fibers are then rinsed, or optionally washed with shampoo, and then dried.

One variant of this process consists, after rinsing and shampooing, in performing a neutralization step using an aqueous hydrogen peroxide solution, and then in rinsing again, optionally washing with shampoo, and then drying.

The application temperature is preferably between room temperature and 60° C. and even more preferably between 35° C. and 50° C.

The time that is sufficient to develop the bleaching of the human keratin fibers is generally between 1 and 60 minutes and even more specifically between 5 and 30 minutes.

According to the present invention, the sulfinic acid derivatives of formula (I) may be combined with at least one α-oxocarboxylic acid or a cosmetically acceptable salt thereof.

A subject of the present invention is thus also a cosmetic composition, characterized in that it comprises, in a cosmetically acceptable medium at a pH of between 1.5 and 9, at least one sulfinic acid. derivative of formula (I) according to the present invention and described above, and at least one α-oxocarboxylic acid or a cosmetically acceptable salt thereof.

The α-oxocarboxylic acids are especially chosen from oxalic acid, glyoxalic acid, pyruvic acid and, preferably, α-ketoglutaric acid.

The cosmetically acceptable salts of these acids are preferably the alkali metal or alkaline-earth metal salts.

The α-oxocarboxylic acid(s) or salts thereof may be present in the composition in proportions of between 0.01% and 15% and preferably between 0.1% and 10% by weight relative to the total weight of the composition.

Preferably, care will be taken to ensure that the weight ratio between the sulfinic acid(s) of formula (I), or the salts thereof, and the α-oxocarboxylic acid(s), or the salts thereof, is between 10/1 and 1/10.

A subject of the invention is also a composition for bleaching keratin fibers died with oxidation dyes and/or direct dyes, in particular human keratin fibers such as the hair, comprising at least one dye-reducing agent in an aqueous medium that is suitable for bleaching at a pH of between 1.5 and 9, and characterized in that said reducing agent is a system combining (i) at least one sulfinic acid derivative of formula (I) and (ii) at least one α-oxocarboxylic acid, or a cosmetically acceptable salt thereof.

The example that follows is intended to illustrate the invention without, however, limiting its scope.

EXAMPLE

The composition below was prepared:

| | |
|---|---|
| Sulfinic acid derivative of formula (I)* | 10.8 mM |
| Sodium olefin sulfonate | 0.25 g |
| Orthophosphoric acid. . . qs. . . pH | 2.7 |
| Water. . . qs | 100 g |

*

$$\text{Na O}-\overset{\overset{O}{\|}}{S}-\overset{\overset{OH}{|}}{\underset{\underset{COO\,Na}{|}}{C}}-(CH_2)_2COO\,Na$$

Locks of hair were dyed beforehand with a commercial oxidation dye Majirouge Nuance 6.66.

They were then bleached by immersion for 30 minutes in the solution of the above example, at a rate of 10 g of solution per 1 g of treated hair. After rinsing with water and shampooing, they were treated for three minutes with aqueous 6% hydrogen peroxide solution, at a rate of 10 g of solution per 1 g of treated hair. After rinsing with water, shampooing and drying, they were bleached with return to the initial shade and lost their red glint.

The bleaching performance was evaluated by measuring the ΔE bleaching of the hair using a Minolta CM 2002 colorimeter in the CIE L*a*b* international system. According to this system, the higher the value of L, the lighter or less intense the color. Conversely, the lower the value of L, the darker or more intense the color [L*=0 is black; L*=100 is white].

a* and b* indicate two color axes, a* indicates the green/red color axis (+a* is red, −a* is green) and b* indicates the blue/yellow color axis (+b* is yellow and −b* is blue).

Values close to zero for a* and b* correspond to gray shades.

The ΔE bleaching is calculated by applying the following equation:

$$\Delta E = \sqrt{(L^* - L_0^*)^2 + (a^* - a_0^*)^2 + (b^* - b_0^*)^2}$$

In this equation, ΔE represents the difference in color between two locks (in the present case, the bleaching), L*, a* and b* represent, respectively, the measurements of the bleached lock, $L_0^*$, $a_0^*$ and $b_0^*$ represent, respectively, the measurements of the control lock before it is dyed.

The lower the value of ΔE, the lesser the color difference between the two locks, and, in the present case, the greater the bleaching.

On an average of three dyed locks, the results were as follows:

| | |
|---|---|
| Mean ΔE | 24.8 |
| Standard deviation | 1.3 |

What is claimed is:

1. A cosmetic composition comprising, in a cosmetically acceptable medium at a pH ranging from 1.5 to 9, at least one compound chosen from sulfinic acid derivatives of formula (I) below and cosmetically acceptable salts thereof:

$$X'O-\overset{\overset{O}{\|}}{S}-\overset{\overset{Y}{|}}{\underset{\underset{(CH_2)_mCOOX}{|}}{C}}-(CH_2)_nCOOX \quad (I)$$

in which:

X, and X', which may be identical or different, are chosen from a hydrogen atom, monovalent metal ions, and ionic equivalents of divalent metals from groups Ia, IIa, IIb, IVa and VIIIb of the Periodic Table of Elements;

Y is chosen from an OH radical, a radical $NR_1R_2$ in which $R_1$ and $R_2$, which may be identical or different, are chosen from a hydrogen atom and $C_1$–$C_6$ alkyl radicals; and n and m, which may be identical or different, are chosen from integers ranging from 0 to 2.

2. The composition of claim 1, wherein:

X and X', which may be identical or different, are chosen from a hydrogen atom, alkali metal ions, and ionic equivalents of alkaline-earth metals or of zinc;

Y is chosen from an OH radical and an $NH_2$ radical; and m=0, and n=0, 1, or 2.

3. The composition of claim 2, wherein:

X and X', which are identical, are the ion Na; and

Y is an OH radical.

4. The composition of claim 1, further comprising at least one α-oxocarboxylic acid or a cosmetically acceptable salt thereof.

5. The composition of claim 4, wherein the α-oxocarboxylic acid is α-ketoglutaric acid or an alkali metal or alkaline-earth metal salt thereof.

6. The composition of claim 4, wherein the α-oxocarboxylic acid is chosen from oxalic acid, glyoxalic acid, pyruvic acid, and an alkali metal or alkaline-earth metal salt thereof.

7. A method for bleaching human keratin fibers dyed with oxidation dyes and/or direct dyes, comprising applying to said keratin fibers a cosmetic composition comprising, in a cosmetically acceptable aqueous medium at a pH ranging from 1.5 to 9 and suitable for bleaching said keratin fibers, at least one compound chosen from sulfinic acid derivatives of formula (I) below and cosmetically acceptable salts thereof:

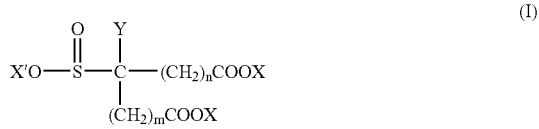

in which:
X, and X', which may be identical or different, are chosen from a hydrogen atom, monovalent metal ions, and ionic equivalents of divalent metals from groups Ia, IIa, IIb, IVa and VIIIb of the Periodic Table of Elements;
Y is chosen from an OH radical, a radical $NR_1R_2$ in which $R_1$ and $R_2$, which may be identical or different, are chosen from a hydrogen atom and $C_1$–$C_6$ alkyl radicals; and
n and m, which may be identical or different, are chosen from integers ranging from 0 to 2.

8. The method of claim 7, wherein the pH of said aqueous medium ranges from 1.8 to 6.

9. The method of claim 7, wherein said keratin fibers are human hair.

10. A composition for bleaching human keratin fibers dyed with oxidation dyes and/or direct dyes comprising at least one dye-reducing agent in an aqueous cosmetic medium that is suitable for bleaching said dyed fibers at a pH ranging from 1.5 to 9, and wherein said at least one dye-reducing agent is chosen from sulfinic acid derivatives of formula (I) below and the cosmetically acceptable salts thereof:

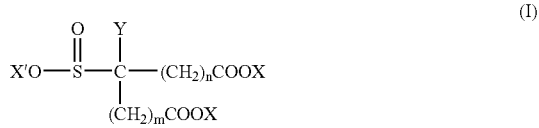

in which:
X, and X', which may be identical or different, are chosen from a hydrogen atom, a monovalent metal ion or an ionic equivalent of a divalent metal from groups Ia, IIa, IIb, IVa and VIIIb of the Periodic Table of Elements;
Y is chosen from an OH radical, a radical $NR_1R_2$ in which $R_1$ and $R_2$, which may be identical or different, denote a hydrogen atom or a $C_1$–$C_6$ alkyl radical; and
n and m, which may be identical or different, denote an integer from 0 to 2.

11. The composition of claim 10, wherein said keratin fibers are human hair.

12. The composition of claim 10, wherein said at least one dye-reducing agent is combined with at least one α-oxocarboxylic acid, or a cosmetically acceptable salt thereof.

13. The composition of claim 10, wherein the pH of said aqueous medium ranges from 1.8 to 6.

14. The composition of claim 10, wherein the at least one dye-reducing agent is present in an amount ranging from 0.01% to 20% by weight relative to the total weight of the composition.

15. The composition of claim 14, wherein the at least one dye-reducing agent is present in an amount ranging from 0.1 % to 10% by weight relative to the total weight of the composition.

16. The composition of claim 10, further comprising at least one thickener.

17. The composition of claim 16, wherein said at least one thickener is chosen from cellulose derivatives, guar derivatives, gums of microbial or plant origin, and synthetic thickeners.

18. The composition of claim 16, wherein the at least one thickener is present in an amount ranging from 0.01 % to 10% by weight relative to the total weight of the composition.

19. The composition of claim 10, further comprising at least one acidifying or basifying agent in an amount ranging from 0.01 % to 30% by weight relative to the total weight of the composition.

20. The composition of claim 19, wherein said at least one acidifying agent is chosen from mineral and organic acids.

21. The composition of claim 20, wherein said at least one acidifying agent is chosen from etidronic acid, hydrochloric acid, orthophosphoric acid, carboxylic acids, and sulfonic acids.

22. The composition of claim 21, wherein the carboxylic acids are chosen from tartaric acid, citric acid, and lactic acid.

23. The composition of claim 19, wherein said basifying agent is chosen from aqueous ammonia, alkaline carbonates, alkanolamines, 2-methyl2-amino-1-propanol and derivatives thereof, sodium hydroxide, potassium hydroxide and the compounds of formula (III) below:

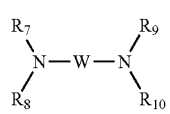

in which:
W is a propylene residue optionally substituted with a hydroxyl group or a $C_1$–$C_4$ alkyl radical; and
$R_7$, $R_8$, $R_9$ and $R_{10}$, which may be identical or different, are chosen from a hydrogen atom, $C_1$–$C_4$ alkyl radicals, and $C_1$–$C_4$ hydroxyalkyl radicals.

24. The composition of claim 23, wherein said alkanolamines are chosen from monoethanolamine, diethanolamine and triethanolamine.

25. A method for making a composition for bleaching human keratin fibers that have been dyed with oxidation dyes and/or direct dyes, said method comprising
extemporaneous mixing, at the time of application to said keratin fibers, of
an anhydrous composition comprising at least one compound chosen from sulfinic acid derivatives of formula (I) below and cosmetically acceptable salts thereof:

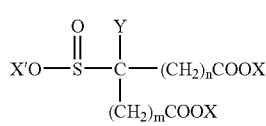

in which:
- X, and X', which may be identical or different, are chosen from a hydrogen atom, monovalent metal ions, and ionic equivalents of divalent metals from groups Ia, IIa, IIb, IVa and VIIIb of the Periodic Table of Elements;
- Y is chosen from an OH radical, a radical $NR_1R_2$ in which $R_1$ and $R_2$, which may be identical or different, are chosen from a hydrogen atom and $C_1$–$C_6$ alkyl radicals; and
- n and m, which may be identical or different, are chosen from integers ranging from 0 to 2, and
- an aqueous composition at a pH ranging from 1.5 to 9.

26. The method of claim 25, wherein said aqueous composition is at a pH ranging from 1.8 to 6.

27. A method for making a composition for bleaching human keratin fibers that have been dyed with oxidation dyes and/or direct dyes, said method comprising
- extemporaneous mixing, at the time of application to said keratin fibers, of
  - an first aqueous composition comprising, at acidic or alkaline pH, at least one compound chosen from sulfinic acid derivatives of formula (I) below and cosmetically acceptable salts thereof:

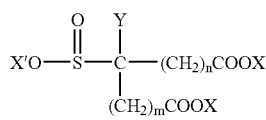

in which:
- X, and X', which may be identical or different, are chosen from a hydrogen atom, monovalent metal ions, and ionic equivalents of divalent metals from groups Ia, IIa, IIb, IVa and VIIIb of the Periodic Table of Elements;
- Y is chosen from an OH radical, a radical $NR_1R_2$ in which $R_1$ and $R_2$, which may be identical or different, are chosen from a hydrogen atom and $C_1$–$C_6$ alkyl radicals; and
- n and m, which may be identical or different, are chosen from integers ranging from 0 to 2, and
- a second aqueous composition at acidic pH.

28. The composition of claim 10, wherein said composition is in the form of a gel, a cream, a mousse, a solution, or an emulsion.

29. A multi-compartment device for (i) dyeing and then (ii) bleaching human keratin fibers dyed with oxidation dyes and/or direct dyes, comprising
- a first compartment comprising at least one dyeing composition chosen from compositions for oxidation dyeing and compositions for direct dyeing of said fibers, and
- a second compartment comprising a composition for the reductive bleaching of said dyed fibers comprising, at a pH ranging from 1.5 to 9, at least one compound chosen from sulfinic acid derivatives of formula (I) below and cosmetically acceptable salts thereof:

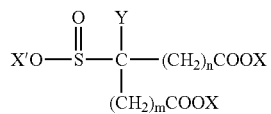

in which:
- X, and X', which may be identical or different, are chosen from a hydrogen atom, monovalent metal ions, and ionic equivalents of divalent metals from groups Ia, IIa, IIb, IVa and VIIIb of the Periodic Table of Elements;
- Y is chosen from an OH radical, a radical $NR_1R_2$ in which $R_1$ and $R_2$, which may be identical or different, are chosen from a hydrogen atom and $C_1$–$C_6$ alkyl radicals; and
- n and m, which may be identical or different, are chosen from integers ranging from 0 to 2.

30. The device of claim 29, wherein the composition for oxidation dyeing comprises at least one oxidation base and/or at least one coupler, wherein said at least one base and/or at least one coupler form an oxidation dye by mixing with at least one oxidizing agent.

31. The device of claim 29, wherein the first compartment comprises both at least one oxidation dye and at least one direct dye.

32. The device of claim 31, wherein the at least one direct dye is chosen from cationic direct dyes, which form a lightening direct dye by mixing with an oxidizing agent.

33. The device of claim 29, wherein the direct dyeing composition comprises at least one direct dye chosen from cationic direct dyes.

34. The device of claim 33, wherein said cationic direct dyes are chosen from the dyes of structures (I) to (VII) below, and the mesomeric forms thereof:

(i) dyes of formulae (I), (II)a, (II)b, (III)a and (III)b:

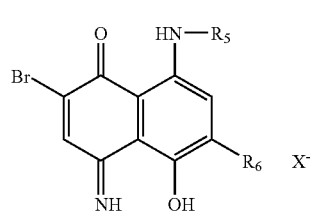

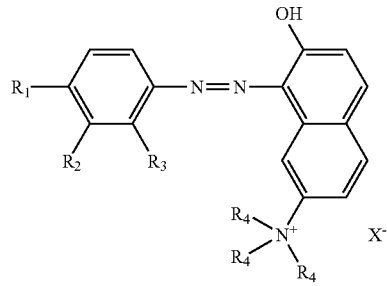

-continued

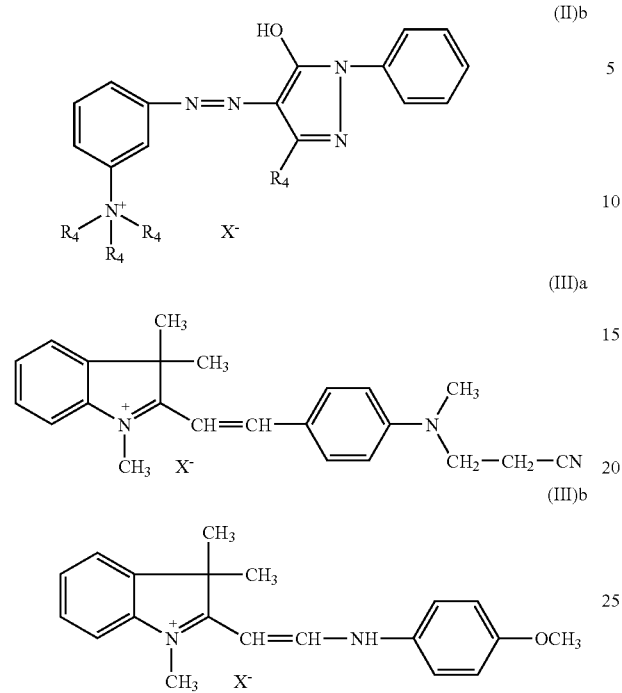

in which formulae (I), (II)a, (II)b, (III)a and (III)b:
R₁ is chosen from a hydrogen atom and an amino radical;
R₂ is chosen from a hydrogen atom and a nitro group;
R₃ is chosen from a hydrogen atom, a nitro group, and a C₁–C₄ alkoxy radical;
R₄ is chosen from a C₁–C₄ alkyl radical;
R₅ is chosen from a hydrogen atom and a para-tri(C₁–C₄) alkyl-ammoniophenyl group;
R₆ is chosen from a bromine atom and an NH-para-tri (C₁–C₄) alkylammoniophenyl group;
X⁻ is an anion;
(ii) dyes of formulae (IV), (V), (VI), (VI') and (VII):
a) the compounds of formula (IV):

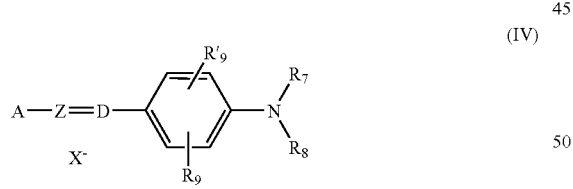

in which:
Z and D, which may be identical or different, are chosen from a nitrogen atom and a —CH— radical;
R₇ and R₈, which may be identical or different, are chosen from a hydrogen atom, a 4'-aminophenyl radical, and C₁–C₄ alkyl radicals which may be substituted with a —CN, —OH or —NH₂ radical, or form, with a carbon atom of the benzene ring, a heterocycle optionally containing oxygen or nitrogen, and which may be substituted with at least one C₁–C₄ alkyl radical;
R₉ and R'₉, which may be identical or different, are chosen from a hydrogen atom, a halogen atom, a cyano radical, C₁–C₄ alkyl radicals, C₁–C₄ alkoxy radicals, and C₁–C₄ acetyloxy radicals;

X⁻ is an anion; and
A is a group chosen from structures A1 to A19 below:

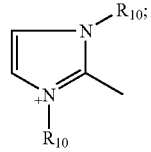   A₁

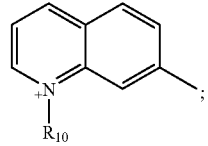   A₂

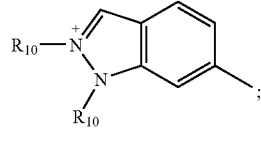   A₃

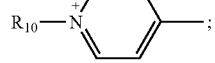   A₄

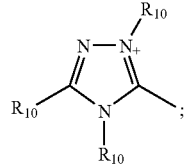   A₅

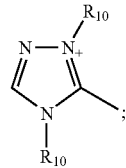   A₆

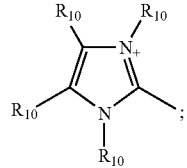   A₇

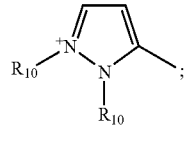   A₈

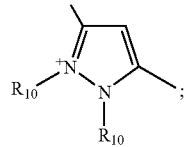   A₉

-continued b) the compounds of formula (V) below:

$$B-N=N-\underset{R_{15}}{\overset{R_{14}}{\underset{|}{\bigcirc}}}-N\underset{R_{13}}{\overset{R_{12}}{\diagdown}} \quad X^- \qquad (V)$$

in which:

R$_{12}$ is chosen from a hydrogen atom and a C$_1$–C$_4$ alkyl radical;

R$_{13}$ is chosen from a hydrogen atom, an alkyl radical which may be substituted with a —CN radical or with an amino group, a 4'-aminophenyl radical, or forms with R$_{12}$ a heterocycle optionally comprising at least one heteroatom chosen from oxygen and nitrogen, and which may be substituted with a C$_1$–C$_4$ alkyl radical;

R$_{14}$ and R$_{15}$, which may be identical or different, are chosen from a hydrogen atom, a halogen atom, C$_1$–C$_4$ alkyl radicals, C$_1$–C$_4$ alkoxy radicals, and a —CN radical;

X$^-$ is an anion; and

B is a group chosen from structures B1 to B6 below:

in which:

R$_{10}$ is an C$_1$–C$_4$ alkyl radical which may be substituted with a hydroxyl radical; and R$_{11}$ is a C$_1$–C$_4$ alkoxy radical;

in which:

R$_{16}$ is a C$_1$–C$_4$ alkyl radical; and $R_{17}$ and $R_{18}$, which may be identical or different, are chosen from a hydrogen atom and a $C_1$–$C_4$ alkyl radical;

c) the compounds of formulae (VI) and (VI') below:

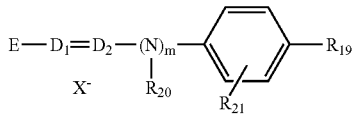 (VI)

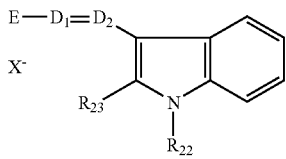 (VI')

in which:

$R_{19}$ is chosen from a hydrogen atom, a $C_1$–$C_4$ alkoxy radical, a halogen atom and an amino radical;

$R_{20}$ is chosen from a hydrogen atom, a $C_1$–$C_4$ alkyl radical, or forms, with a carbon atom of the benzene ring, a heterocycle optionally comprising oxygen and/or optionally substituted with at least one $C_1$–$C_4$ alkyl group;

$R_{21}$ is chosen from a hydrogen atom and a halogen atom;

$R_{22}$ and $R_{23}$, which may be identical or different, are chosen from a hydrogen atom and a $C_1$–$C_4$ alkyl radical;

$D_1$ and $D_2$, which may be identical or different, are chosen from a nitrogen atom and a —CH group;

m=0 or 1;

$X^-$ is an anion; and

E is a group chosen from structures E1 to E8 below:

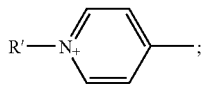 E1

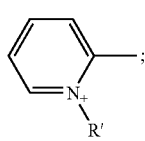 E2

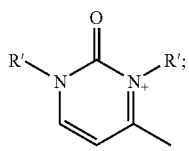 E3

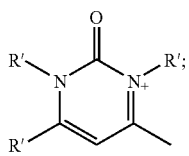 E4

-continued

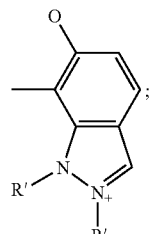 E5

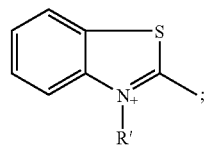 E6

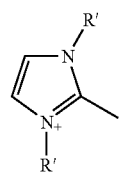 E7 and

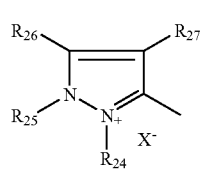 E8 in which:

R' is a $C_1$–$C_4$ alkyl radical; and when m=0 and $D_1$ is a nitrogen atom, then E may also denote a group of structure E9 below:

E9 in which:

R' is a $C_1$–$C_4$ alkyl radical;

d) the compounds of formula (VII) below:

G—N=N—J  (VII)

in which:

G is a group chosen from the structures $G_1$ to $G_3$ below:

$G_1$

-continued

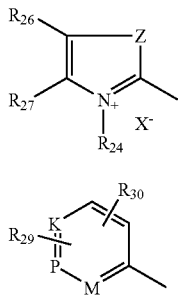

G₂

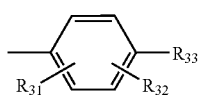

G₃ in which:
- R₂₄ is chosen from a $C_1$–$C_4$ alkyl radical, a phenyl radical which may be substituted with a $C_1$–$C_4$ alkyl radical, and a halogen atom chosen from chlorine, bromine, iodine and fluorine;
- R₂₅ is chosen from a $C_1$–$C_4$ alkyl radical and a phenyl radical;
- R₂₆ and R₂₇, which may be identical or different, are chosen from a $C_1$–$C_4$ alkyl radical, a phenyl radical, or form together in G₁ a benzene ring substituted with at least one radical chosen from $C_1$–$C_4$ alkyl, $C_1$–$C_4$ alkoxy and NO₂ radicals, or form together in G₂ a benzene ring optionally substituted with at least one radical chosen from $C_1$–$C_4$ alkyl, $C_1$–$C_4$ alkoxy and NO₂ radicals;
- R₂₆ may also denote a hydrogen atom;
- Z is chosen from an oxygen atom, a sulfur atom and a group —NR₂₅;
- M is chosen from groups —CH, —CR, wherein R is a $C_1$–$C_4$ alkyl radical, and —NR₂₈(X⁻)ᵣ;
- K is chosen from groups —CH, —CR, wherein R is a $C_1$–$C_4$ alkyl radical, and —NR₂₈(X⁻)ᵣ;
- P is chosen from groups —CH, —CR, wherein R is a $C_1$–$C_4$ alkyl radical, and —NR₂₈(X⁻)ᵣ;
- r is 0 or 1;
- R₂₈ is chosen from an O⁻ atom, a $C_1$–$C_4$ alkoxy radical and a $C_1$–$C_4$ alkyl radical;
- R₂₉ and R₃₀, which may be identical or different, are chosen from a hydrogen atom, a halogen atom, a $C_1$–$C_4$ alkyl radical, a $C_1$–$C_4$ alkoxy radical, and an —NO₂ radical;
- X⁻ is an anion; and
- J is chosen from:
  - (a) a group of structure J₁ below:

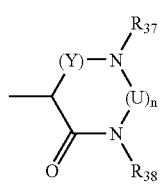

J₁ in which:
- R₃₁ is chosen from a hydrogen atom, a halogen atom, a $C_1$–$C_4$ alkyl radicals, a $C_1$–$C_4$ alkoxy radical, —OH, —NO₂, —NHR₃₄, —NR₃₅R₃₆ and $C_1$–$C_4$ —NH-COalkyl radicals, or forms with R₃₂ a 5- or 6-membered ring optionally containing one or more hetero atoms chosen from nitrogen, oxygen and sulfur;
- R₃₂ represents a hydrogen atom, a halogen atom, a $C_1$–$C_4$ alkyl or $C_1$–$C_4$ alkoxy radical, or forms with R₃₃ or R₃₄ a 5- or 6-membered ring optionally comprising at least one hetero atom chosen from nitrogen, oxygen and sulfur;
- R₃₃ is chosen from a hydrogen atom, an —OH radical, a radical —NHR₃₄ and a radical —NR₃₅R₃₆;
- R₃₄ is chosen from a hydrogen atom, a $C_1$–$C_4$ alkyl radical, a $C_1$–$C_4$ monohydroxyalkyl radical, a $C_2$–$C_4$ polyhydroxyalkyl radical and a phenyl radical;
- R₃₅ and R₃₆, which may be identical or different, are chosen from a $C_1$–$C_4$ alkyl radical, a $C_1$–$C_4$ monohydroxyalkyl radical, and a $C_2$–$C_4$ polyhydroxyalkyl radical;
- (b) a 5- or 6-membered nitrogenous heterocyclic group, which may contain other hetero atoms and/or carbonyl groups and may be substituted with at least one radical chosen from $C_1$–$C_4$ alkyl, amino and phenyl radicals.

35. A device of claim 34, wherein said 5- or 6-membered nitrogenous heterocyclic group, which may contain other hetero atoms and/or carbonyl groups and may be substituted with at least one radical chosen from $C_1$–$C_4$ alkyl, amino and phenyl radicals, is a group of structure J₂ below:

J₂ in which:
- R₃₇ and R₃₈, which may be identical or different, are chosen from a hydrogen atom, a $C_{13}$–$C_{10}$ alkyl radical, and a phenyl radical;
- Y is chosen from a —CO— radical and a $$-\underset{|}{\overset{CH_3}{C}}=$$

radical;
- n=0 or 1, wherein, when n is 1, U is a —CO— radical.

36. The device of claim 34, wherein said cationic direct dye is chosen from the structures that correspond to (IV1), (IV2), (IV14) and (IV31) of formula (IV):

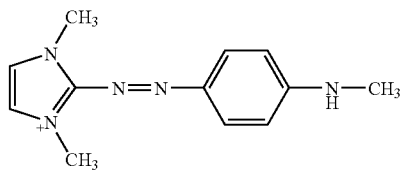

(IV1)

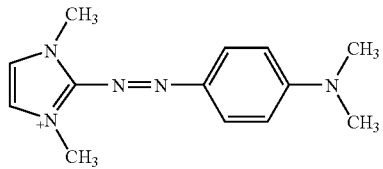

(IV2)

-continued

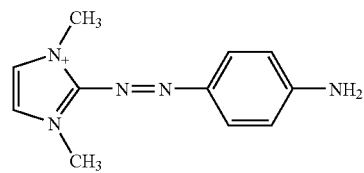

(IV14)

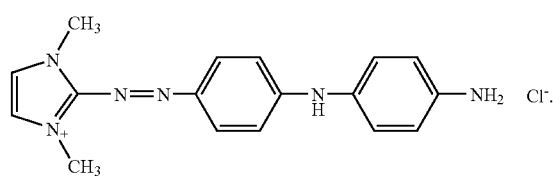

(IV31)

37. A process for bleaching human keratin fibers dyed with oxidation dyes and/or direct dyes, comprising applying to said fibers, at an application temperature ranging from room temperature to 80° C. and for a time sufficient to partially or totally strip the dye from the hair, a composition comprising, in a cosmetically acceptable medium at a pH ranging from 1.5 to 9, at least one compound chosen from sulfinic acid derivatives of formula (I) below and cosmetically acceptable salts thereof:

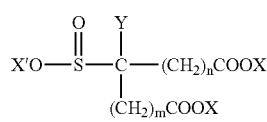 (I)

in which:
X, and X', which may be identical or different, are chosen from a hydrogen atom, monovalent metal ions, and ionic equivalents of divalent metals from groups Ia, IIa, IIb, IVa and VIIIb of the Periodic Table of Elements;
Y is chosen from an OH radical, a radical $NR_1R_2$ in which $R_1$ and $R_2$, which may be identical or different, are chosen from a hydrogen atom and $C_1$–$C_6$ alkyl radicals; and n and m, which may be identical or different, are chosen from integers ranging from 0 to 2.

38. The process of claim 37, wherein the application temperature ranges from 35° C. to 50° C.

39. The process of claim 37, wherein the time sufficient to partially or totally strip the dye from the hair ranges from 1 to 60 minutes.

40. The process of claim 39, wherein the time ranges from 5 to 30 minutes.

41. A compound of formula (I):

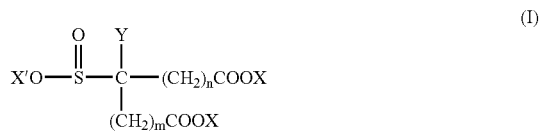 (I)

in which:
X and X', which may be identical or different, are chosen from a hydrogen atom, a monovalent metal ion, and an ionic equivalent of a divalent metal from groups Ia, IIa, IIb, IVa and VIIIb of the Periodic Table of Elements;
Y is chosen from an OH radical, a radical $NR_1R_2$ in which $R_1$ and $R_2$, which may be identical or different, are chosen from a hydrogen atom and a $C_1$–$C_6$ alkyl radical; and
n and m, which may be identical or different, are integers ranging from 0 to 2.

42. The compound of claim 41, in which:
X and X', which may be identical or different, are chosen from a hydrogen atom, an alkali metal ion, and an ionic equivalent of an alkaline-earth metal or of zinc;
Y is chosen from an OH radical and an $NH_2$ radical; and
m=0, and n=0, 1, 2.

43. The compound of claim 42, in which:
X and X', which are identical, denote the ion Na; and
Y is an OH radical.

* * * * *

UNITED STATES PATENT AND TRADEMARK OFFICE
CERTIFICATE OF CORRECTION

PATENT NO.        : 7,179,300 B2
APPLICATION NO.   : 10/489733
DATED             : February 20, 2007
INVENTOR(S)       : Frédéric Legrand et al.

It is certified that error appears in the above-identified patent and that said Letters Patent is hereby corrected as shown below:

In claim 23, column 66, line 40, "2-methyl2-amino-l-propanol" should read

--2-methyl-2-amino-l-propanol--.

In claim 26, column 67, line 24, "1.8to6." should read --1.8 to 6.--.

In claim 27, column 67, line 30, "an first" should read --a first--.

In claim 34, column 71, line 65, "an $C_1$-$C_4$ alkyl radical" should read
--a $C_1$-$C_4$ alkyl radical--.

In claim 34, column 75, lines 60-61, "a $C_1$-$C_4$ alkyl radicals," should read
--a $C_1$-$C_4$ alkyl radical,--.

In claim 36, column 77, lines 1-9,

" 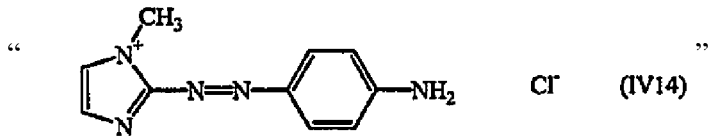 "

should read

-- 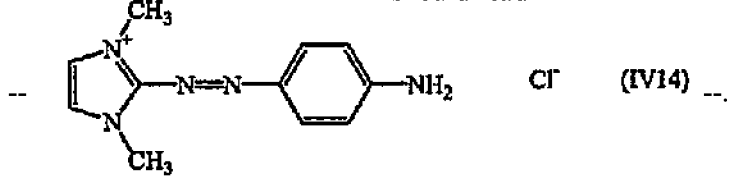 --.

Signed and Sealed this

Eighth Day of May, 2007

JON W. DUDAS
*Director of the United States Patent and Trademark Office*